(12) United States Patent
Flaherty et al.

(10) Patent No.: US 11,517,471 B2
(45) Date of Patent: *Dec. 6, 2022

(54) APPARATUS AND METHODS FOR THE TREATMENT OF SLEEP APNEA

(71) Applicant: Lumen Devices, LLC, Stamford, CT (US)

(72) Inventors: J. Christopher Flaherty, Auburndale, FL (US); John T. Garibotto, Marblehead, MA (US); William J. Gorman, S. Hamilton, MA (US); John N. Irwin, III, Greenwich, CT (US); Michael Friedman, Lincolnwood, IL (US)

(73) Assignee: LUMEN DEVICES, LLC., Stamford, CT (US)

( * ) Notice: Subject to any disclaimer, the term of this patent is extended or adjusted under 35 U.S.C. 154(b) by 207 days.

This patent is subject to a terminal disclaimer.

(21) Appl. No.: 16/851,218

(22) Filed: Apr. 17, 2020

(65) Prior Publication Data
US 2021/0085514 A1 Mar. 25, 2021

Related U.S. Application Data

(63) Continuation of application No. 15/611,085, filed on Jun. 1, 2017, now Pat. No. 10,660,787, which is a
(Continued)

(51) Int. Cl.
*A61F 5/56* (2006.01)
(52) U.S. Cl.
CPC .................................. *A61F 5/566* (2013.01)

(58) Field of Classification Search
CPC ... A61F 5/566; A61F 5/56; A61F 5/00; A61B 1/233; A61M 16/0497; A61M 16/00; A61M 16/0463; Y10S 602/902; A63B 71/085; A63B 2071/088; A63B 2071/086; A63B 2225/09; A63B 2209/08; A63B 2220/51;
(Continued)

(56) References Cited

U.S. PATENT DOCUMENTS 3,132,647 A 5/1964 Corniello
4,598,707 A 7/1986 Agdanowski et al.
(Continued)

FOREIGN PATENT DOCUMENTS

DE 19501363 9/1995
EP 0418391 3/1991
(Continued)

OTHER PUBLICATIONS

Canadian Office Action dated Sep. 6, 2016 issued in corresponding Canadian Application No. 2,911,748.
(Continued)

*Primary Examiner* — Ophelia A Hawthorne
(74) *Attorney, Agent, or Firm* — Onello & Mello, LLP

(57) ABSTRACT

A medical apparatus for the treatment of one or more sleep disorders such as obstructive sleep apnea in a patient is provided. The apparatus has an elongate member with a middle portion, a first fixation element and a second fixation element. The middle portion applies a force to a segment of a patient's airway.

15 Claims, 21 Drawing Sheets

Related U.S. Application Data continuation of application No. 13/985,977, filed as application No. PCT/US2012/025458 on Feb. 16, 2012, now Pat. No. 9,668,911.

(60) Provisional application No. 61/443,839, filed on Feb. 17, 2011.

(58) Field of Classification Search
CPC ..... A63B 2213/00; A63B 71/10; A63B 23/03; A63B 23/032
See application file for complete search history.

(56) References Cited

U.S. PATENT DOCUMENTS

| | | |
|---|---|---|
| 4,669,459 A | 6/1987 | Spiewak et al. |
| 4,778,448 A | 10/1988 | Meer |
| 4,883,465 A | 11/1989 | Brennan |
| 4,901,737 A | 2/1990 | Toone |
| 5,092,346 A | 3/1992 | Hays et al. |
| 5,103,807 A | 4/1992 | Makaran |
| 5,352,209 A | 10/1994 | Bird et al. |
| 5,395,309 A | 3/1995 | Tanaka et al. |
| 5,403,980 A | 4/1995 | Eckrich |
| 5,938,582 A | 8/1999 | Ciamacco, Jr. et al. |
| 6,048,073 A | 4/2000 | Shiao |
| 6,102,929 A | 8/2000 | Conway et al. |
| 6,117,386 A | 9/2000 | Stiger |
| 6,273,859 B1 | 8/2001 | Remmers et al. |
| 6,275,724 B1 | 8/2001 | Dickinson et al. |
| 6,312,138 B1 | 11/2001 | Coleman, Jr. et al. |
| 6,394,093 B1 | 5/2002 | Lethi |
| 6,408,852 B2 | 6/2002 | Tielemans |
| 6,591,049 B2 | 7/2003 | Williams et al. |
| 6,605,056 B2 | 8/2003 | Eidenschink et al. |
| 6,734,893 B1 | 5/2004 | Hess et al. |
| 6,770,263 B1 | 8/2004 | Brucker |
| 6,916,287 B2 | 7/2005 | Dematteis et al. |
| 6,932,084 B2 | 8/2005 | Estes et al. |
| 6,955,172 B2 | 10/2005 | Nelson et al. |
| 7,278,751 B2 | 10/2007 | Chang et al. |
| 7,347,209 B2 | 3/2008 | Bovo |
| 7,381,222 B2 | 6/2008 | Pflueger et al. |
| 7,410,480 B2 | 8/2008 | Muni et al. |
| 7,451,766 B2 | 11/2008 | Miller |
| 7,547,296 B2 | 6/2009 | Lampropoulos et al. |
| 7,654,997 B2 | 2/2010 | Makower et al. |
| 7,658,192 B2 | 2/2010 | Harrington |
| 7,686,021 B2 | 3/2010 | Knudson et al. |
| 7,686,824 B2 | 3/2010 | Konstantino et al. |
| 7,771,447 B2 | 8/2010 | Kunis |
| 7,810,176 B2 | 10/2010 | Turner |
| 7,815,661 B2 | 10/2010 | Mirizzi et al. |
| 7,834,287 B2 | 11/2010 | Heiman et al. |
| 7,861,722 B2 | 1/2011 | Keropian |
| 7,879,061 B2 | 2/2011 | Keith et al. |
| 7,887,661 B2 | 2/2011 | Chiu et al. |
| 7,914,468 B2 | 3/2011 | Shalon et al. |
| 8,127,769 B2 | 3/2012 | Walker |
| 8,146,600 B2 | 4/2012 | Pflueger et al. |
| 8,302,609 B2 | 11/2012 | Martinez |
| 8,403,881 B2 | 3/2013 | Ferren et al. |
| 8,678,008 B2 | 3/2014 | Rousseau et al. |
| 8,684,007 B2 | 4/2014 | Timmons |
| 8,739,794 B2 | 6/2014 | Cutler |
| 8,894,614 B2 | 11/2014 | Muni et al. |
| 8,978,647 B2 | 3/2015 | Djupesland et al. |
| 9,132,028 B2 | 9/2015 | Friedman et al. |
| 9,526,856 B2 | 12/2016 | Azagury et al. |
| 9,668,911 B2 | 6/2017 | Flaherty et al. |
| 10,022,262 B2 | 7/2018 | Irwin et al. |
| 10,441,457 B2 | 10/2019 | Friedman et al. |
| 10,660,787 B2 * | 5/2020 | Flaherty ............... A61F 5/566 |
| 2001/0027793 A1 | 10/2001 | Tielemans |
| 2002/0009275 A1 | 1/2002 | Williams et al. |
| 2003/0014007 A1 | 1/2003 | Eidenschink et al. |
| 2003/0121519 A1 | 7/2003 | Estes et al. |
| 2004/0020492 A1 | 2/2004 | Dubrul et al. |
| 2004/0049102 A1 | 3/2004 | Nelson et al. |
| 2004/0138585 A1 | 7/2004 | Dematteis et al. |
| 2004/0143287 A1 | 7/2004 | Konstantino et al. |
| 2004/0194785 A1 | 10/2004 | Miller |
| 2005/0137618 A1 | 6/2005 | Kunis |
| 2005/0203366 A1 | 9/2005 | Donoghue et al. |
| 2005/0240147 A1 | 10/2005 | Makower et al. |
| 2005/0268919 A1 | 12/2005 | Knudson et al. |
| 2006/0064037 A1 | 3/2006 | Shalon et al. |
| 2006/0106361 A1 | 5/2006 | Muni et al. |
| 2006/0130850 A1 | 6/2006 | Chen |
| 2006/0169285 A1 | 8/2006 | Bovo |
| 2006/0195135 A1 | 8/2006 | Ayoub |
| 2006/0229669 A1 | 10/2006 | Mirizzi et al. |
| 2007/0008715 A1 | 1/2007 | Chang et al. |
| 2007/0066942 A1 | 3/2007 | Lampropoulos et al. |
| 2007/0103451 A1 | 5/2007 | Heiman et al. |
| 2007/0129751 A1 | 6/2007 | Muni et al. |
| 2007/0255198 A1 | 11/2007 | Leong et al. |
| 2008/0015497 A1 | 1/2008 | Keith et al. |
| 2008/0035158 A1 | 2/2008 | Pflueger et al. |
| 2008/0035160 A1 | 2/2008 | Woodson et al. |
| 2008/0041396 A1 | 2/2008 | Lucker |
| 2008/0041516 A1 | 2/2008 | Chiu et al. |
| 2008/0051871 A1 | 2/2008 | Tuch |
| 2008/0058584 A1 | 3/2008 | Hirotsuka et al. |
| 2008/0065209 A1 | 3/2008 | Pflueger et al. |
| 2008/0076094 A1 | 3/2008 | Hindin |
| 2008/0078412 A1 | 4/2008 | Buscemi et al. |
| 2008/0091067 A1 | 4/2008 | Dollar |
| 2008/0210244 A1 | 9/2008 | Keropian |
| 2008/0289637 A1 | 11/2008 | Wyss |
| 2009/0084388 A1 | 4/2009 | Bagley et al. |
| 2009/0157056 A1 | 6/2009 | Ferren et al. |
| 2009/0204099 A1 | 8/2009 | Feloney |
| 2009/0281433 A1 | 11/2009 | Saadat et al. |
| 2010/0024830 A1 | 2/2010 | Rousseau et al. |
| 2010/0198249 A1 | 8/2010 | Sabliere |
| 2010/0211009 A1 | 8/2010 | Leonard et al. |
| 2010/0268025 A1 | 10/2010 | Belson |
| 2010/0282246 A1 | 11/2010 | Djupesland et al. |
| 2010/0319708 A1 | 12/2010 | Mahr et al. |
| 2011/0178439 A1 | 7/2011 | Irwin et al. |
| 2011/0226264 A1 | 9/2011 | Friedman et al. |
| 2013/0046329 A1 | 2/2013 | Burbank et al. |
| 2013/0312768 A1 | 11/2013 | Flaherty et al. |
| 2014/0000622 A1 | 1/2014 | Azagury et al. |
| 2015/0342779 A1 | 12/2015 | Friedman et al. |
| 2016/0001022 A1 | 1/2016 | Djupesland et al. |
| 2017/0266034 A1 | 9/2017 | Flaherty et al. |
| 2020/0306474 A1 | 10/2020 | Flaherty et al. |

FOREIGN PATENT DOCUMENTS

| | | |
|---|---|---|
| EP | 2205306 | 7/2010 |
| WO | 2007020197 | 2/2007 |
| WO | 2008122791 | 10/2008 |
| WO | 2010068493 | 6/2010 |
| WO | 2014030078 | 2/2014 |

OTHER PUBLICATIONS

International Preliminary Report on Patentability dated Aug. 29, 2013 corresponding to PCT/US2012/025458, 27pp.

International Search Report and Written Opinion dated Jul. 16, 2012 from PCT/US2012/025458; 41 pages.

"Aparatus and Methods for the Treatment of Sleep Apnea" Specification, Drawings and Prosecution History of U.S. Appl. No. 13/985,977, filed Aug. 16, 2013, now U.S. Pat. No. 9,668,911, issued Jun. 6, 2017, by J. Christopher Flaherty, et al., which is stored in the United States Patent and Trademark Office (USPTO).

"Aparatus and Methods for the Treatment of Sleep Apnea" Specification, Drawings and Prosecution History of U.S. Appl. No. 15/611,085, filed Jun. 1, 2017, now U.S. Pat. No. 10,660,787, issued

(56) References Cited

OTHER PUBLICATIONS

May 26, 2020, by J. Christopher Flaherty, et al., which is stored in the United States Patent and Trademark Office (USPTO).
European Office Action dated Jan. 22, 2021 issued in corresponding European Application No. 15195168.8.

* cited by examiner

FIG 3A  SECTION B-B

FIG 3B  SECTION B-B

FIG 3C  SECTION B-B

SECTION A-A

APPARATUS AND METHODS FOR THE TREATMENT OF SLEEP APNEA

RELATED APPLICATIONS

This application is a continuation application of U.S. patent application Ser. No. 15/611,085, filed on Jun. 1, 2017, now U.S. Pat. No. 10,660,787, issued on May 26, 2020, which is a continuation application of U.S. patent application Ser. No. 13/985,977, filed on Aug. 16, 2013, now U.S. Pat. No. 9,668,911, issued Jun. 6, 2017, which claims the benefit of United States PCT application serial number PCT/US2012/025458, filed on Feb. 16, 2012, now International Publication No.: WO 2012/112783, published on Aug. 23, 2012, which claims the benefit of U.S. Provisional Application No. 61/443,839, filed Feb. 17, 2011, the content of which is incorporated herein by reference in its entirety.

BACKGROUND

1. Field

The present disclosure relates generally to the use of nasally and orally inserted devices for the treatment of patients with one or more sleep disorders, such as sleep apnea or severe snoring. The devices are configured to provide a biasing force to the soft palate or the tongue, such that continuous airflow can be achieved while the patient sleeps.

2. Discussion of the Background Art

The sleep apnea syndrome, and in particular obstructive sleep apnea, afflicts an estimated 2-5% of the general population and is due to episodic upper airway obstruction during sleep. Those afflicted with obstructive sleep apnea experience sleep fragmentation and intermittent, complete or nearly complete cessation of ventilation during sleep with potentially severe degrees of oxyhemoglobin unsaturation. These features may be translated clinically into debilitating daytime sleepiness, cardiac disrhythmias, pulmonary-artery hypertension, congestive heart failure and cognitive dysfunction. Other problems related to sleep apnea include carbon dioxide retention during wakefulness as well as during sleep, and continuous reduced arterial oxygen tension. Hypersomnolent sleep apnea patients may be at risk for excessive mortality from these factors as well as from an elevated risk for accidents such as while driving or operating other potentially dangerous equipment.

Although details of the pathogenesis of upper airway obstruction in sleep apnea patients have not been fully defined, it is generally accepted that the mechanism includes either anatomic or functional abnormalities of the upper airway which result in increased air flow resistance. Such abnormalities may include narrowing of the upper airway due to suction forces evolved during inspiration, the effect of gravity pulling the tongue back to obstruct the pharyngeal wall, and/or insufficient muscle tone in the upper airway dilator muscles. It has also been hypothesized that a mechanism responsible for the known association between obesity and sleep apnea is excessive soft tissue in the anterior and lateral neck which applies sufficient pressure on internal structures to narrow the airway.

One theory of the cause for the sleep disturbance is the relaxation of the tongue and pharyngeal walls to varying degrees during the several stages of sleep. When fully awake, these tissues have normal tone as air passes in and out of the lungs during respiration. However, during sleep, the musculature supporting these tissues relaxes. As air is inspired, the tongue and posterior walls of the pharynx collapse, causing snoring or, more seriously, partial or complete obstruction of the airway.

Obstructive sleep apnea occurs due to a collapse of soft tissue within the upper airway during sleep.

Apnea is the term for suspension of breathing. During apnea there is no movement of the muscles of respiration.

The ongoing force of inspiration serves to generate increasingly negative pressure within the pharynx, causing further collapse. The lack of respiration results in inadequate blood oxygenation, and rising carbon dioxide levels. The cardiovascular response produces an increase in the blood pressure and pulse. One or more cardiac arrhythmias often occur. The carbon dioxide increase and oxygen desaturation triggers a transition to a lighter sleep stage, usually without wakefulness. This transition brings a return to tonicity of the muscles of the upper airway, allowing normal breathing to resume. The person then returns to deeper stages of sleep and the process is repeated. The disease is quantified in terms of respiratory disturbances per hour. Mild disease begins at 2-3 APNEAS per hour, and it is not uncommon to find patients with indices of 75 or more.

Not surprisingly, sleep is extremely fragmented and of poor quality in persons suffering from sleep apnea. As a result, such persons typically feel tired upon wakening and may fall asleep at inappropriate times during the day. All aspects of quality of life, from physical and emotional health, to social functioning are impaired by obstructive sleep apnea.

Surgical Treatments

The treatment of sleep apnea has included such surgical interventions as Uvulopalatopharyngoplasty (UPPP) gastric surgery for obesity, and maxillo-facial reconstruction. Another mode of surgical intervention used in the treatment of sleep apnea is tracheostomy. These treatments constitute major undertakings with considerable risk of post-operative mortality. In UPPP, any remaining tonsil tissue and a portion of soft palate is removed. The procedure often increases the nasopharyngeal airway. However, UPPP does not always fix a sagging soft palate nor does it address apnea caused by obstructions caused by the base of the tongue being deeper in the oropharynx region of the airway. These surgical techniques are extremely invasive, requiring general anesthesia, and a prolonged, painful recovery.

LAUP, or Laser-Assisted Uvulopalatoplasty, is a modification of the above-mentioned technique, but has had mixed success and cannot solve obstructions behind the base of the tongue.

Radiofrequency tissue ablation (RFTA) with the trade name "Somnoplasty", has been used to shrink the soft palate, uvula and reduce tongue volume in the treatment of snoring and obstructive sleep apnea. Somnoplasty utilizes a radiofrequency tool that generates heat to create coagulative lesions at specific locations within the upper airway. The lesions created by the procedure are naturally resorbed in approximately three to eight weeks, reducing excess tissue volume and increasing the airway opening. More than one session is typically required, and other surgeries may still be necessary in moderate to severe cases, and there are occasional problems with morbidity.

Another area of surgical interest lies in techniques designed to pull the tongue in an anterior direction. The most recent such surgical system designed to treat snoring (as well as obstructive sleep apnea) was approved by the FDA in February 1998. Known as the tongue suspension procedure (with the trade name Repos™), it is intended to pull the tongue forward, thereby keeping the tongue from falling into the airway during sleep. The system utilizes a bone screw inserted into the mandible. The screw attaches to a non-absorbable suture which travels the length of the tongue and back. Similarly, the hyoid bone can be drawn anteriorly with two distinct screws, also attached to the mandible.

Techniques have also been developed for treating, specifically, the condition of snoring. Conrad et al., U.S. Pat. No. 6,250,307 discloses a method for treating snoring of a patient, which includes embedding an implant into a soft palate of a patient in order to alter a dynamic response of a soft palate to airflow. The methods of Conrad et al. are specifically designed to reduce the audibility of snoring but do not address the more serious condition of sleep apnea.

These conventional treatments continue to suffer poor or partial cure rates. The failures lie in their inability to maintain patency in the retropalatal region and retroglossal region (the caudal margin of the soft palate to the base of the epiglottis). The poor success rates combined with high morbidity from some of the surgical interventions, contribute to an ongoing need for more effective treatments for sleep apnea and/or snoring.

Pharmacological Treatments

Pharmacological therapy aimed at stimulating upper airway muscle to reduce apneas also have, in general, been disappointing. In addition, side effects from the pharmacological agents that have been used are frequent. Thus, medical practitioners continue to seek non-invasive modes of treatment for sleep apnea with high success rates and high patient compliance including, for example in cases of minor to moderate sleep apnea relating to obesity, weight loss through a regimen of exercise and regulated diet.

Other Non-Surgical Treatments

Other non-surgical treatments for sleep apnea include the use of oral devices and appliances that work to prevent the tongue from falling backwards or help reduce the collapse of the soft palate. These involve the use of retainers that push the lower jaw forward, thereby pulling the tongue slightly forward and, in some cases, helping elevate the soft palate. Also, there are devices that pull on the tongue to keep it forward during sleep. These current oral devices typically do not create a significant improvement except in mild to moderate cases and can be associated with movement of the teeth over time causing problems with the temporomandibular joint.

Recent work in the treatment of sleep apnea has included the use of continuous positive airway pressure (CPAP) to maintain the airway of the patient in a continuously open state during sleep, CPAP by delivering a stream of air under pressure through the nose or mouth stents the airway (keeping it open) so that apneas are reduced and breathing during sleep becomes unobstructive.

For example, U.S. Pat. No. 4,655,213 and Australian patent AU-B-83901/82 both disclose sleep apnea treatments based on continuous positive airway pressure applied within the airway of the patient.

Also of interest is U.S. Pat. No. 4,773,411 which discloses a method and apparatus for ventilatory treatment characterized as airway pressure release ventilation which provides a substantially constant elevated airway pressure with periodic short term reductions of the elevated airway pressure to a pressure magnitude no less than ambient atmospheric pressure.

Although CPAP has been found to be very effective and well accepted, it suffers from some of the same limitations, although to a lesser degree, as do the surgical options; specifically, a significant proportion of sleep apnea patients do not tolerate CPAP well. Thus, development of other viable non-invasive therapies has been a continuing objective in the art.

Still others have attempted to solve sleep apnea disorders using intraorally fitted appliances, including U.S. Pat. Nos. 4,981,437 and 4,932,867, which disclose a method and apparatus for constructing dentures, which are useful, for example, in treating breathing disorders. U.S. Pat. No. 4,386,405 discloses a device for measuring the location, attitude, or change of location of a patient's lower jaw. U.S. Pat. No. 4,859,181 relates to optical measurement of jaw movement. U.S. Pat. Nos. 3,998,209 and 4,220,142 disclose conditioning systems for use in a program of behavior modification to eliminate snoring, while U.S. Pat. No. 4,976,618 relates to treatment of temporomandibular joint dysfunction and bruxism. U.S. Pat. No. 3,297,021 discloses an intraoral strain gauge and telemetering of information from an intraoral location to an outside indicator.

The following U.S. patents purport to relate to tongue positioning and/or retaining apparatus: U.S. Pat. Nos. 5,154,184; 5,092,346; 5,046,512; 4,676,240; 4,169,473; 4,304,227 and 4,593,686. Other patents addressing the matter of tongue positioning include the following: U.S. Pat. Nos. 5,649,540; 5,465,734; 5,373,859; 5,052,409; 4,715,368; 4,196,724; 3,884,226; 3,312,216 and 3,132,647, as well as European patent 0182387 and British patent 874,480. The following patents purport to relate to chin straps or similar apparatus intended to hold the jaw closed: U.S. Pat. Nos. 3,312,217; 2,711,730 and 1,990,411.

Other patents relate to apparatus for interaction with the soft palate in the user's oral cavity. These include U.S. Pat. Nos. 4,669,459 and 5,316,020, German patent no. DE 40 26 602 and European patent no. EP 0264516. Other patents of general interest include U.S. Pat. Nos. 5,056,534 and 2,705,006, German patent nos. 65194 and 2320501, and PCT publication no. WO 92/05752 and European patent application no. 0 487 469 A1.

While the above-identified conventional devices and surgical techniques are purported to treat upper airway instability, such as obstructive sleep apnea (OSA) or snoring, they are successful, if at all, in only a limited pool of patients or under limited circumstances. While CPAP therapy has had significant success in reducing or eliminating apneas through the delivery of air under pressure, CPAP treatment suffers from patient non-compliance and cannot be tolerated by an ample minority of patients. Therefore, there remains a relatively large number of patients whose airway disorder is believed to be treatable using an intraoral appliance, yet conventional appliances are ineffective, overly burdensome, uncomfortable, or any combination thereof.

There is therefore a need for improved airway scaffolding apparatus to provide continuous or semi-continuous flow of air through the nasopharynx. The present disclosure also provides many additional advantages, which shall become apparent as described below.

SUMMARY

The present disclosure comprises an apparatus used to scaffold the airway of a patient suffering from a sleep disorder, for example, sleep apnea. Additionally, a method of using an airway scaffolding apparatus is disclosed. The apparatus is configured to apply a force to the airway of a patient to enhance the flow of air and prevent airway occlusion. The airway comprises the area proximate the soft palate, base of a patient's tongue, nasal passageway, or another location along a patient's airway.

According to a first aspect of the disclosure, an apparatus comprising an elongate member, a first fixation element, such as a nosepiece, and a second fixation element, such as a mouthpiece, is provided. The elongate member may comprise a single filament having a proximal portion, a middle portion, and a distal portion. The distal portion of the elongate member may include one or more filaments, and may comprise a continuous loop. Preferably, a cross section of the elongate member, such as a cross section configured to apply a force to a soft palate or tongue of a patient, comprises a width between about 0.005 inches and 0.350 inches, and more preferably, between about 0.020 inches and 0.110 inches. The elongate member may be comprised of different cross sectional geometries, such as cross sections including an oval, circular and/or rectangular geometry. The elongate member may have varying cross sections along its length. The elongate member may comprise a hollow portion and/or a solid portion. Preferably, the elongate member comprises at least a portion with a Shore A durometer less than or equal to about 75, preferably less than about 60, and more preferably, less than about 50. In some embodiments, the elongate member may have a varying rigidity along its length. For example, the distal portion may be more rigid than the proximal portion, such as to assist in the insertion of the distal portion into the nostril and through the airway of a patient. The elongate member may have a varying modulus of elasticity along its length.

The elongate member may be constructed of materials selected from the group consisting of: silicone; polyethylene; polyurethane; pebax; elastomer; shaped memory material such as shaped memory metal or shaped memory polymer material; thermoplastic; plastic; and combinations of these. In one embodiment, the elongate member comprises a shaped memory component which may be positioned on the interior and/or exterior surface of the elongate member. For example, the elongate member mid portion may comprise a shaped memory metal or a shaped memory polymer that is configured to increase rigidity after placement, change shape after placement, and/or apply a force to a patient's soft palate after placement.

In some embodiments, the elongate member may comprise a coating. For example, the elongate member may be coated with an analgesic, a decongestant, an antihistamine, and/or a lubricant or other friction reducing coating.

In one embodiment, the elongate member comprises at least two filaments. For example, in the case of two filaments, a user may insert a filament into each nostril and independently attach the two filaments via the filament distal ends to the second fixation element.

In one embodiment, the elongate member comprises a distal portion configured to be inserted into the nostril of a patient and to exit the patient's mouth. The distal portion, or a sub-portion, may be removed after insertion into the patient. For example, the distal end may be cut via a cutting element, such as a cutting element located on the second fixation element. The distal portion of the elongate member may comprise a capture section configured to be captured via a capturing element configured to assist the patient or another operator in feeding the elongate member through the nasal passageway, into and then out of the mouth. The capture section may comprise a magnetic portion such as a magnetic material such as a ferrous material, or a magnet such as an electromagnet. The capture section may also include, but is not limited to a Velcro component; a loop portion; an adhesive or otherwise tacky portion; and combinations of these. In some embodiments, the distal portion may comprise a rigid section, for example, the section comprising the capture element may be rigid.

In one embodiment, the elongate member middle portion has a greater thickness than the thickness of the elongate member's proximal and/or distal portions. The middle portion may comprise a diameter between about 0.10 inches and 0.80 inches, and more preferably between about 0.35 inches and 0.45 inches. The middle portion may comprise one or more sections with a Shore A durometer of less than about 60, preferably less than about 50, and more preferably less than about 40.

In one embodiment, the middle portion comprises an expandable member, for example, a balloon or cage configured to radially expand. For example, the first fixation element may comprise a control, such as a slidable rod or a fluid delivering syringe, configured to cause the radial expansion of the expandable member. Alternatively, the middle portion may comprise a shaped memory component, such as a Nitinol component, configured to automatically expand when exposed to a rise in temperature (e.g., a rise from room temperature to an internal body temperature). The shaped memory component may transition into a helix or other radially expanded or curvilinear geometry. The middle portion may comprise a solid cylinder and/or a hollow tube having a circular, oval, and/or rectangular cross section. In an alternate embodiment, the middle portion may comprise at least two filaments. A membrane, such as a mesh or a porous sheet, may be positioned between the two filaments. The membrane may comprise a flexible material such as a silicone elastomer and may comprise a surface area greater than 4 $mm^2$, and more preferably greater than 10 $mm^2$. In another embodiment, the middle portion may comprise a ribbon having an approximate aspect ratio of about 5.

In some embodiments, the elongate member may include a coated or treated portion, typical coatings including but not limited to: a lubricant or other friction reducing coating or treatment; a hydrophilic or hydrophobic coating, a surface modification such as a surface energy modification; a therapeutic compound, such as an analgesic, a decongestant, and/or an antihistamine; and combinations of these.

In a typical embodiment, the elongate member may be configured to be tensioned to apply a force to the soft palate, base of a patient's tongue, or another location along a patient's airway. The force applied may be to a full or partial circumference of a patient's airway, and is typically accomplished by the mid portion of the elongate member. The tensioning of the elongate member may be achieved via the first fixation element and/or the second fixation element. In one embodiment, two independently tensionable filaments are positioned on either side of a patient's uvula.

In an alternate embodiment, the apparatus may comprise a second elongate member configured to apply a force to a second portion of the airway of a patient. For example, a first elongate member may apply a force to a patient's soft palate, while the second elongate member applies a force to the base of a patient's tongue.

The apparatus of the present disclosure comprises a first fixation element, such as a nosepiece configured to secure and adjust the tension of the elongate member. The first fixation element may be configured to tension and/or adjust the tension of the elongate member via a tensioning assembly selected from the group consisting of: a ratchet mechanism; a frictional engagement element such as a notch or groove sized to capture the elongate member; a roller clamp or pinch clamp assembly; a tubing clamp; a cleat; Velcro;

and combinations of these. The nosepiece may comprise a nostril plug, may be positioned flush with a patient's nostril, and/or may comprise a nasal dilator. Additionally, the nosepiece may comprise a coating, such as a coating including one or more of: an antibiotic; an antihistamine; an analgesic; and combinations of these. In one embodiment, the nosepiece comprises a first control configured to activate an expandable element located on the elongate member. In addition, a second control may be configured to reverse the activation of the expandable element. Alternatively, the first control may comprise the second control, or the second control may be included in the first control. In some embodiments, the nosepiece may be collapsible.

The apparatus of the present disclosure also comprises a second fixation element, such as a mouthpiece, which may also be configured to secure and adjust the tension of the elongate member. The mouthpiece may include one or more tensioning mechanisms such as a tension assembly selected from the group consisting of: a ratchet mechanism; a frictional engagement element such as a notch or groove sized to capture the elongate member; a roller clamp or pinch clamp assembly; a tubing clamp; a cleat; Velcro; and combinations of these.

In one embodiment, the mouthpiece may be custom sized to a patient, which may be done by the patient or a clinician. For example, the mouthpiece may be sized by heating the mouthpiece and inserting it into the patient's mouth, allowing plastic deformation of at least a portion of the mouthpiece. The mouthpiece may be attached to the patient's upper and/or lower jaw, or it may be attached to a tooth or teeth, directly or indirectly. The mouthpiece may include a cutting element, for example a sharp edge configured to cut the distal portion of the elongate member after the distal portion has been secured to the mouthpiece. In one embodiment, the mouthpiece may comprise a guide assembly configure to guide a tool, such as a tool configured to capture a portion of the elongate member. For example, the guide assembly may comprise a slot configured to receive the distal portion of the elongate member after it has been captured by the tool, such as a magnetic tool.

In an alternative embodiment, the second fixation may comprise a tissue penetrating or piercing element, for example a tongue piercing element.

In yet another alternate embodiment, the second fixation element is configured to wrap around the soft palate inferior edge. For example, the distal end of the elongate member may comprise a hook-like construction configured to removably engage the inferior edge of the soft palate. In this embodiment, the elongate member may have a malleability and flexibility sufficient to allow flexing during removal from the soft palate.

The apparatus may include a filament capture probe configured to grasp the distal portion of the elongate member. The probe may have a tongue depressor construction, and may capture a capture element such as a magnet included in the elongate member. Capturing mechanisms may include, but are not limited to: magnets, grasping jaws, adhesives; Velcro™; suction elements and combinations of these. The probe may further comprise a light emitting element such as a light emitting diode (LED). In one embodiment, the LED may be positioned to direct light toward the posterior side of the patient's airway when inserted into the patient's mouth. Alternatively or additionally, the LED may be positioned to direct light in a superior direction when inserted into a patient's mouth. The probe may further comprise a switch to control the LED. The switch may be activated in various ways including but not limited to: manually; upon contact with tissue such as the patient's tongue; contact with saliva; pressure activation; and combinations of these. The switch may be a latching switch configured to remain illuminated after initial activation.

The apparatus may include an analgesic agent, for example an analgesic spray applied to a portion of the patient's airway prior to insertion of the apparatus. The agent is configured to improve patient comfort during the insertion of the elongate member into a patient's airway. The analgesic spray may be used during or after insertion of the apparatus.

According to another aspect of the disclosure, a method of inserting an airway scaffolding apparatus is disclosed. The method comprises inserting an elongate member, including proximal, middle and distal portions, into an airway of a patient. A force is applied to a portion of the airway by at least the middle portion of the elongate member. In one embodiment, a user (e.g., the patient or clinician) may insert the distal portion of the elongate member through a patient's nostril and into the airway. In an alternate embodiment, the elongate member may be inserted into a patient's mouth and then into the airway. In some embodiments, the elongate member comprises a loop construction, and the user may position a first portion of the loop on one side of the patient's uvula and a second portion of the loop on the other side of the uvula. In another embodiment, the user may position the loop around a periphery of a jaw fixation element.

The method may include a user inserting a nasal fixation element, such as a nosepiece, into the nostril of the patient and attaching the elongate member to the nosepiece. Additionally, the user may insert a second nosepiece. Subsequently, the user may tension the elongate member via the first and/or second nosepiece, such as via a tensioner included in a nosepiece and/or a jaw fixation element. Tensioners may include, but are not limited to: a ratchet mechanism; a frictional engagement element such as a notch or groove sized to capture the elongate member; a roller clamp or pinch clamp assembly; a tubing clamp; a cleat; Velcro™; and combinations of these.

The method further includes a user inserting a jaw fixation element, such as a mouthpiece, in the patient's mouth and attaching the fixation element, such as by attaching to the upper and/or lower jaw. The elongate member may be attached to the mouthpiece, such as via a slot or groove, and the tension may be adjusted to achieve a desired force applied to the patient's airway. The distal portion of the elongate member may be attached automatically or manually. In one embodiment, the user captures the distal portion of the elongate member via a probe, such as a probe including a magnet when the distal portion includes a magnetic element. The capture section may also include, but is not limited to a Velcro component; a loop portion; an adhesive or otherwise tacky portion; and combinations of these. Prior to this step, a user may size the mouthpiece, for example, via a warm water mold.

In some embodiments, the user may deploy and expand an expandable element, such as an expandable element positioned behind the soft palate or base of the tongue. This expansion may be achieved by fluid expansion, retraction or advancement of a rod or other deployment arm, and/or shaped memory material expansion via body heat.

In another embodiment, a user may remove the distal end of the distal portion of the elongate member, such as via cutting, tearing, and/or overcoming a frictional engagement force. Alternatively or additionally, the user may separate the distal end of the elongate member into two filaments.

In yet another embodiment, a user may apply an analgesic to at least a portion of a patient's airway prior to, during or after insertion of the apparatus into the patient's airway.

Further objects, features and advantages of the present disclosure will be understood by reference to the following drawings and detailed description.

BRIEF DESCRIPTION OF THE DRAWINGS

The accompanying drawings, which are incorporated in and constitute a part of this specification, illustrate various embodiments of the present disclosure, and together with the description, serve to explain the principles of the disclosure. In the drawings:

FIGS. 3A-3C illustrate cross-sectional views of a scaffolding assembly of the present disclosure;

DETAILED DESCRIPTION OF THE PREFERRED EMBODIMENT

Reference will now be made in detail to the present embodiments of the disclosure, examples of which are illustrated in the accompanying drawings. Wherever possible, the same reference numbers will be used throughout the drawings to refer to the same or like parts.

Figure 1:
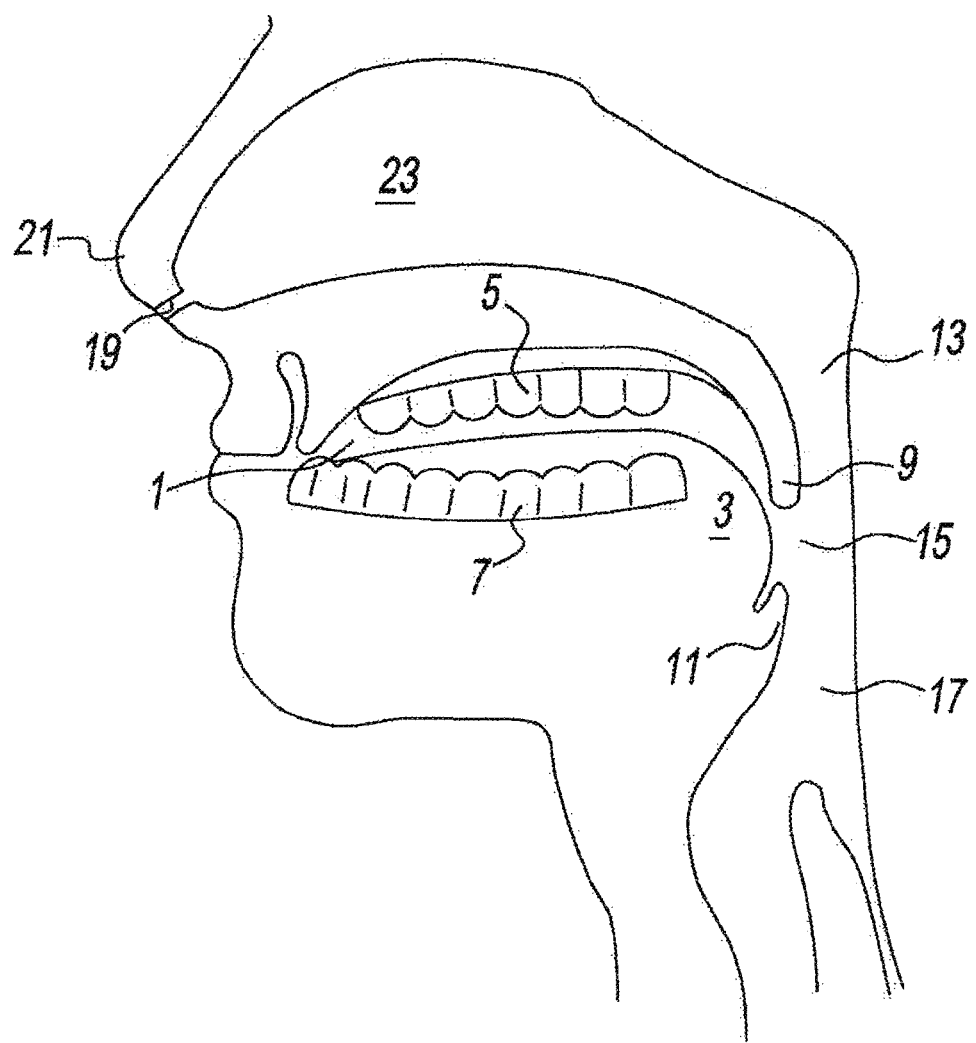
FIG. 1 illustrates is a cross-sectional view of a patient's soft palate, oral cavity and pharynx without any apparatus disposed therein.

Referring now to FIG. 1, a cross-section of a patient's oral cavity is illustrated. Oral cavity 1 includes a tongue 3, upper jaw 5, lower jaw 7, soft palate 9, and epiglottis 11, as well as the nasopharynx region 13, oropharynx region 15 and laryngopharynx region 17. In addition, nasal valve 19 and nose 21 having a nasal passageway 23 to connect nasal valve 19 with nasopharynx region 13.

Figure 2:
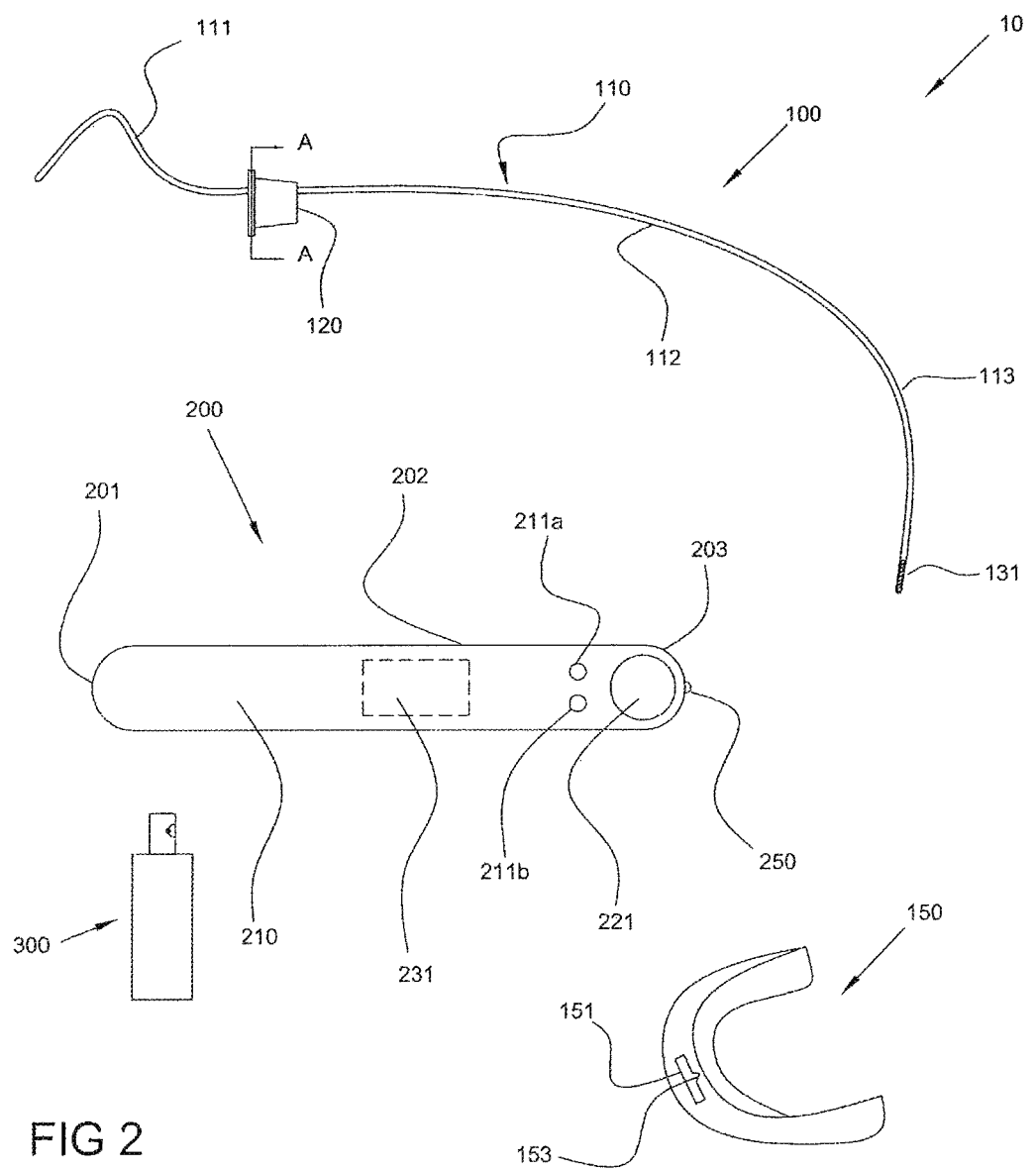
FIG. 2 illustrates a schematic view of an apparatus for scaffolding a nasopharyngeal airway, consistent with the current disclosure.

Referring now to FIG. 2, an airway scaffolding apparatus including a scaffolding assembly, a capture probe and a jaw attachment assembly is illustrated. Airway scaffolding apparatus 10 is typically a nightly use device for a patient suffering from sleep apnea or other airway occlusive disorder. In one embodiment, airway scaffolding apparatus 10 is disposed of each morning, after a single night's use. Airway scaffolding apparatus 10 includes a scaffolding filament, scaffolding assembly 100, constructed and arranged to apply a force to a portion of an airway, such as at a location behind the soft palate, at the base of the tongue, within the nasal passageway, and/or at another airway location. Apparatus 10 may further include a jaw attachment assembly, mouthpiece 150, and a filament capture device, probe 200. Scaffolding assembly 100 is constructed and arranged to be inserted into the nasal passageway of a patient, through the patient's nostril, and to remain in place while a patient sleeps. Alternatively or additionally, scaffolding assembly 100 may be advanced into the nasal passageway through the mouth. In this method, a filament capture device, typically inserted through a nostril, can be used to capture scaffolding assembly 100 and withdraw a portion of scaffolding assembly 100 through the patient's nostril.

Probe 200 is constructed and arranged to be inserted into the patient's mouth, and to capture a distal portion of scaffolding assembly 100, such as to subsequently attach a distal portion of scaffolding assembly 100 to mouthpiece 150. Mouthpiece 150 is designed to be removably fixed to the patient's upper or lower jaw, and stabilize a distal portion of scaffolding assembly 100 such that scaffolding assembly 100 applies a scaffolding force to the patient's soft palate. Apparatus 10 may further include an analgesic agent, such as an analgesic provided in analgesic delivery device 300. Delivery device 300 is constructed and arranged to spray or otherwise deliver an analgesic to a patient airway, such as via a nostril or the patient's mouth.

Scaffolding assembly 100 comprises an elongate member, shaft 110, having proximal portion 111, distal portion 113, and mid portion 112. Mid portion 112 applies a force to a portion of an airway, such as tissue of a patient's soft palate or the base of a patient's tongue, and is positioned between proximal portion 111 and distal portion 113 of shaft 110. Shaft 110 may be comprised of various materials such as materials selected from the group consisting of: silicone, polyethylene, polyurethane, elastomer, shape memory material, thermoplastic, pebax, and combinations of these. Shaft 110 is constructed of materials to allow patient comfort when inserted, yet of sufficient rigidity to apply adequate force to the patient's soft palate or other airway location to prevent occlusion of the airway. In a typical embodiment, at least a portion of shaft 110 has a durometer of less than 75 Shore A, more typically less than 60 Shore A. In one embodiment, at least a portion of shaft 110 has a durometer less than 50 Shore A. In a typical embodiment, at least a portion of mid portion 112 has a durometer of less than 60 Shore A, more typically less than 50 Shore A. In one embodiment, at least a portion of mid portion 112 has a durometer less than 40 Shore A. When in place in the patient's airway, shaft 110 is designed to flex or stretch, such as to accommodate swallowing.

Distal portion 113 may be constructed and arranged to introduce mid portion 112 through the nostril of a patient. Distal portion 113 may comprise a more rigid construction than mid portion 112 such as a construction that is thicker and/or includes different materials than mid portion 112. In one embodiment, distal portion 113 comprises a loop. In another embodiment, distal portion 113 has a round cross section and mid portion 112 has a flat cross section such as a rectangular or oval cross section. Distal portion 113 may be configured to be removed after insertion, such as with a cutting tool or when distal portion 113 includes a weakened or otherwise treated location configured to be separated from mid portion 112.

Shaft 110 has a length sufficient to be positioned from a nostril of the patient, to a location distal to the patient's soft palate. Shaft 110 lengths are typically at least 10 cm, more typically at least 15 cm, and even more typically at least 20 cm. Shaft 110 may comprise a circular cross section with typical outer diameters ranging from about 0.002 inches to 0.350 inches, more typically about 0.020 inches to 0.110 inches. In one embodiment, shaft 110 comprises a circular cross section with a diameter of approximate about 0.050 inches. Shaft 110 may include a non-circular cross section such as an oval or rectangular cross section with a major axis length ranging from about 0.005 inches to 0.350 inches, more typically about 0.020 inches to 0.110 inches. In one embodiment, shaft 110 has an oval cross section with a major axis length between about 0.020 inches and 0.350 inches. In some embodiments, mid portion 112 has a different geometry than proximal portion 111 and/or distal portion 113, such as a geometry with a larger surface area configured to apply a force to the patient's airway. Shaft 110 may include materials that soften over time, such as to be rigid for insertion, and less rigid to achieve patient comfort once in place. Typical materials include liquid absorbing materials such as materials configured to absorb saliva.

In another embodiment, shaft 110 may include a coated or treated portion, typical coatings including but not limited to: a lubricant or other friction reducing coating or treatment; a hydrophilic or hydrophobic coating, a surface modification such as a surface energy modification; a therapeutic compound, such as an analgesic, a decongestant, and/or an antihistamine; and combinations of these.

Mid portion 112 has a length and width sufficient to provide adequate force in the patient's airway to prevent tissue collapse or another sleep apnea event. Mid portion 112 may comprise a ribbon construction, or a cross sectional profile with an aspect ratio greater than about 5, such as to distribute a force over a larger tissue area. Mid portion 112 may comprise one or more filaments, and may include a radially expanding element. Mid portion 112 may comprise a non-circular cross section, such as an oval cross section, with a major axis between about 0.002 inches and 0.350 inches. Mid portion 112 may comprise a circular cross section with a diameter between about 0.020 inches and 0.250 inches, typically approximately about 0.050 inches.

Scaffolding assembly 100 further comprises a nostril fixation element, nosepiece 120, which may be positioned in the nose flush with a nostril of a patient. Nosepiece 120 is constructed and arranged to stabilize the proximal end of shaft 110 in a relatively fixed position. In one embodiment, nosepiece 120 is constructed and arranged to dilate the nasal passageway proximate the nostril. In another embodiment, nosepiece 120 is flexible, such as to be collapsed by the patient to ease in removal after use. Scaffolding assembly 100 may include a second nosepiece 120, for placement in the patient's other nostril. Mouthpiece 150 and/or nosepiece 120 may be constructed and arranged to slidingly pass shaft 110 therethrough, such as to increase or decrease the tension in shaft 110 and subsequently increase or decrease the force applied to the patient's airway. Nosepiece 120 may be constructed and arranged to allow adjustment of the tension of shaft 110, such as to adjust the force applied by mid portion 112 upon the patient's soft palate and/or to adjust for patient comfort such as comfort during swallowing. Nosepiece 120 may include one or more various tensioning mechanisms such as a v-groove or notch sized to capture shaft 110 (described in detail herebelow), a roller clamp assembly or pinch clamp assembly such as tubing clamps used to selectively occlude intravenous tubing sets, a tubing clamp, a cleat, a ratchet mechanism; and combinations of these. These tensioners may be further configured to operable release shaft 110, such as after a nightly use. Nosepiece 120 may comprise a coating, such as a coating including one or more of: an antibiotic; an antihistamine; an analgesic; and combinations of these.

Mouthpiece 150 includes slot 151 and notch 153 which is constructed and arranged to slidingly receive distal portion 113 of shaft 110 and maintain distal portion 113 in a relatively fixed position. Mouthpiece 150 can comprise a retainer, mouth guard, tooth-cap assembly, orthodontic braces, other oral tooth or jaw attachment devices, and combinations of these. In a preferred embodiment, jaw attachment assembly may be configured to be custom sized for a particular patient. Sizing may be performed by a clinician or by a patient and may be achieved by heating jaw attachment assembly 150 (e.g., by placing in a warm-water mold) after which it is placed into the patient's mouth for custom sizing. In an alternative embodiment, the distal end of scaffolding assembly 100 is attached to an anchor implanted in the patient's tongue, such as a tongue piercing device.

In addition to or as an alternative to nosepiece 120, mouthpiece 150 may be constructed and arranged to allow adjustment of the tension of shaft 110, such as to adjust the force applied by mid portion 112 upon the patient's soft palate and/or to adjust for patient comfort such as comfort during swallowing. Mouthpiece 150 may include one or more various tensioning mechanisms such as a notch 153 or v-groove sized to capture shaft 110 (described in detail herebelow), a roller clamp assembly or pinch clamp assembly such as tubing clamps used to selectively occlude intravenous tubing sets, a tubing clamp, a cleat, a ratchet mechanism, and combinations of these. Tensioning mechanisms of mouthpiece 150 may be configured to operably release shaft 110, such as after a nightly use.

In one embodiment, mouthpiece 150 may include a cutting element, not shown but typically one or more sharpened edges configured to cut distal portion 113 of shaft 110 after threading through the slot 151.

Probe 200 comprises tongue depressor 210 having proximal portion 201, medial portion 202, and distal portion 203. Additionally, probe 200 may include at least one LED 250 located on distal portion 203 of tongue depressor 210 which may be used to illuminate such patient locations as the nasopharynx region, the oropharynx region and/or the laryngopharynx region. Contacts 211a and 211b, located on distal portion 203 of tongue depressor 210, are capable of activating LED 250 when contacting tissue or saliva. Power source 231, e.g., a battery, provides power to LED 250.

In a preferred embodiment, probe 200, including magnet 221 located on distal portion 203 of tongue depressor 210, may be inserted through slot 151 of mouthpiece 150. Magnet 221 may then be used to capture magnetic element 131 located on distal portion 113 of shaft 110. Magnetic element 131 is typically a ferrous or other magnetic material of less than about 1 inch in length, more typically less than about 0.5 inches in length. After capture by magnet 221, retraction of probe 200 through slot 151 feeds the distal portion 113 of shaft 110 threaded through slot 151 such that shaft 110 can be captured in notch 153 of mouthpiece 150, and tensioned or otherwise adjusted as desired.

While the distal portion 113 of shaft 110 is attached to mouthpiece 150, which is attached to the patient's jaw, the proximal portion 111 of shaft 110 is attached to nosepiece 120. Nosepiece 120 is frictionally engaged with the patient's nose, and mid portion 112 is positioned and arranged to apply a scaffolding force to the patient's soft palate. As described hereabove, the tension on shaft 110 can be adjusted such as to increase or decrease the scaffolding force applied to the soft palate. Increased force may be necessary to create a sufficiently sized opening to provide adequate airflow for the patient while asleep. A decrease in force may be needed for the patient's comfort, such as to accommodate swallowing, avoid a gag reflex, avoid skin irritation or otherwise be comfortable for the patient.

In an alternative embodiment, magnet 221 may comprise a magnetic material while magnetic material 131 comprises a magnet. In another alternative embodiment, both magnet 221 and magnetic material 131 comprise magnets. Either magnet 221 or magnetic material 131 may comprise electromagnets, such as an electromagnetic assembly which allows the force of attraction between magnet 221 and magnetic material 131 to be adjusted, such as with a control located on mouthpiece 150, not shown but typically including a potentiometer or other electronic componentry configured to adjust the electromagnetic force of magnet 221 and/or magnetic material 131. Alternative or in addition to magnet 221, other capture elements may be included such as: electro-magnets, Velcro™, suction ports, mechanical graspers, adhesive, or combinations of these, each constructed and arranged to capture a corresponding capturable element of the distal end of an elongate member of the present disclosure.

Figure 3:
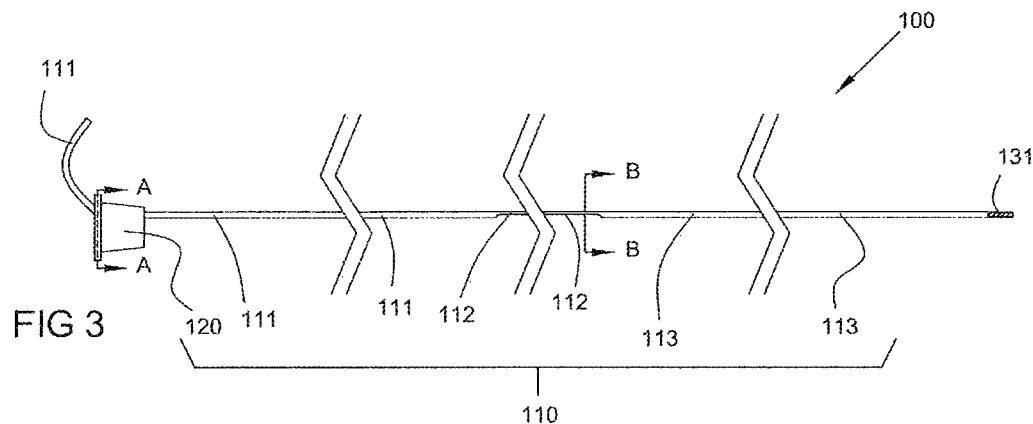
FIG. 3 illustrates a side view of an exemplary embodiment of a scaffolding assembly of the present disclosure.

Referring now to FIG. 3, a side view of a scaffolding assembly of the present disclosure is illustrated including a mid portion with a particular cross-sectional geometry. Scaffolding assembly 100 includes nosepiece 120 on its proximal end and magnetic material 131 on its distal end, such as a magnet or magnetic material configured to be captured by a probe, such as probe 200 of FIG. 2. Scaffolding assembly 100 includes flexible, elongate shaft 110 comprising proximal portion 111, mid portion 112 and distal portion 113. Nosepiece 120 is constructed and arranged to operably engage proximal portion 111. Shaft 110 can be tensioned, such as by frictional engagement with a notch or groove, when attached at its distal end to a securing device such as mouthpiece 150 of FIG. 2 or another device fixed to a location in or proximate to the patient's mouth.

Referring additionally to FIGS. 3A, 3B, and 3C, three alternative cross sections of mid portion 112 (at cross-section B-B as shown in FIG. 3) of scaffolding assembly 100 are illustrated. In a typical embodiment, mid portion 112 has a larger cross sectional area or greater thickness, than either or both proximal portion 111 and distal portion 113. FIG. 3A illustrates a mid portion 112 comprising a hollow tube with an elliptical cross section. FIG. 3B illustrates a mid portion 112 comprising a hollow tube with a circular cross section. FIG. 3C illustrates a mid portion 112 comprising a hollow tube with a rectangular cross section. Based on the anatomical and physiologic differences between patients, various cross-sections of mid portion 112 may be provided such as to improve scaffolding of the individual patient's airway, as well as improve patient comfort. Alternatively or additionally, other portions of shaft 110 may have alternative and/or varied cross sectional profiles. In one embodiment, the cross-sectional geometry within mid portion 112 varies along its length. Mid portion 112 may have a hollow tube construction or a solid tube construction, such as a solid tube with one or more portions having a circular, oval and/or rectangular cross section. To further improve patient comfort, mid portion 112 may be impregnated with one or more agents, such as analgesics. Alternatively, mid portion 112 may include a hollow portion surrounded by porous walls such that one or more analgesic or other agents can be introduced to the portion of the patient's airway in contact with mid portion.

In one embodiment, shaft 110 comprises at least one lumen, such as a lumen configured to support introduction of a fluid, such as air, saline or an agent such as an analgesic, or to slidingly receive a shaft, such as a shaft configured to radially expand or compress a component of scaffolding assembly 100. In an alternative embodiment, shaft 110 is a solid tube. Luminal diameters are chosen to maintain sufficient wall thickness to maintain structural integrity of shaft 110 when shaft 110 is inserted through the patient's nasal passageways as well as to avoid undesired deformation or damage when shaft 110 is under tension. In a preferred embodiment, shaft 110 may comprise a flexible material configured to comfortably apply a force to the soft palate and/or the base of a patient's tongue when scaffolding assembly 100 is inserted into the patient and shaft 110 is placed under tension. Shaft 110 is designed to avoid sharp edges and be constructed of a sufficiently soft and flexible material to achieve patient comfort.

In one embodiment, shaft 110 comprises sections of varying rigidity. For example, distal end 113 may be more rigid (e.g., thicker, made of a different material, or including stiffening elements such as a braid) than proximal end 111 to assist the patient in threading shaft 110 through the nostril. In another embodiment, shaft 110 comprises varying modulus of elasticity from section to section. Mid portion 112 may have a different construction than proximal portion 111 and distal portion 113 such as to provide enhanced scaffolding force to the patient's soft palate. Varying construction may include, but is not limited to, modulus of elasticity of materials, rigidity, cross-sectional profile, thickness, and combinations of these.

In yet another embodiment, shaft 110 may include a flexible mandrel, not shown, but typically a flexible mandrel selected from the group comprising: a shaped memory metal; a shaped memory polymer; a resiliently biased metal filament such as resiliently biased super elastic Nitinol filament (i.e., nickel titanium); and combinations of these. The flexible mandrel is typically positioned within and/or alongside mid portion 112 and configured to increase rigidity and/or increase scaffolding force to the patient's soft palate after placement in the airway. Alternatively or additionally, the flexible mandrel may change shape after placement in the airway, such as when the flexible mandrel is a shaped memory metal configured to change shape as its temperature rises above room temperature.

Shaft 110 may include a coated or treated portion, typical coatings or treatments including but not limited to: a lubricant or other friction reducing coating or treatment; a hydrophilic or hydrophobic coating; a surface modification such as a surface energy modification; a therapeutic compound, such as an analgesic, a decongestant, and/or an antihistamine; and combinations of these.

Figure 4:
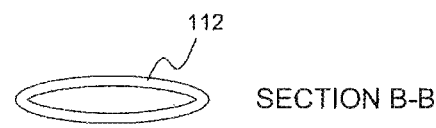
FIG. 4 illustrates a cross-sectional view of a nostril fixation element of the present disclosure in accordance with FIG. 3.
Figure 4:
Figure 4:
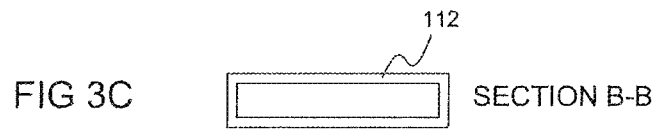
Figure 4:
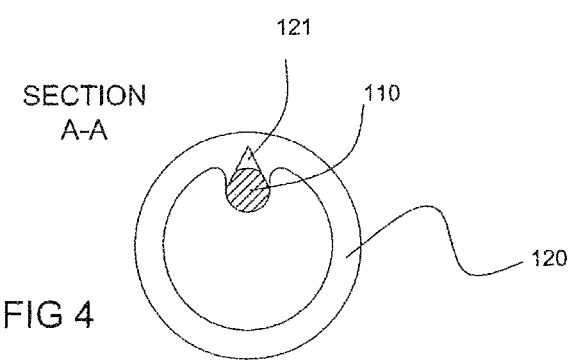

Referring now to FIG. 4, cross section A-A of scaffolding assembly 100 of FIG. 3 is illustrated. Nosepiece 120 may comprise a nostril plug constructed and arranged to frictionally engage with and disengage from a nostril of a patient. Nosepiece 120 may be sized such that it is flush with the nostril of a patient when inserted, and may include a flange, not shown but configured to prevent undesired deep seating of nosepiece 120. Nosepiece 120 may comprise a coating, such as a coating including one or more of: an antibiotic; an antihistamine; an analgesic; and combinations of these.

Nosepiece 120 comprises a filament capturing element, notch 121, which is configured to capture and secure proximal portion 111 of shaft 110. Notch 121 is further configured to allow user adjustable tension to shaft 110. In addition to or as an alternative to a notch, numerous other forms of capture and tensioning elements may be employed including but not limited to: a ratchet mechanism, frictional engagement mechanism such as a v-groove, one or more pinch rollers, and combinations of these; to allow the patient or a separate individual to both secure and adjust the tension of shaft 110, as well as release shaft 110 when apparatus 10 is to be removed after sleep is completed.

In another embodiment, nosepiece 120 comprises a control, not shown but described in various embodiments herebelow. In one embodiment, a control is constructed and arranged to activate a radially expandable element of shaft 110, radially expandable element not shown but typically an inflatable balloon or radially expandable cage. The activatable element positioned on shaft 110 may be configured to expand and/or change the shape of shaft 110 and/or to apply a force to a portion of the patient's airway. A second control may be included, also not shown, to reverse the activation of the middle portion of shaft 110. Alternatively, a single control may be used to both activate and reverse the activity of the middle portion.

Figure 5A:
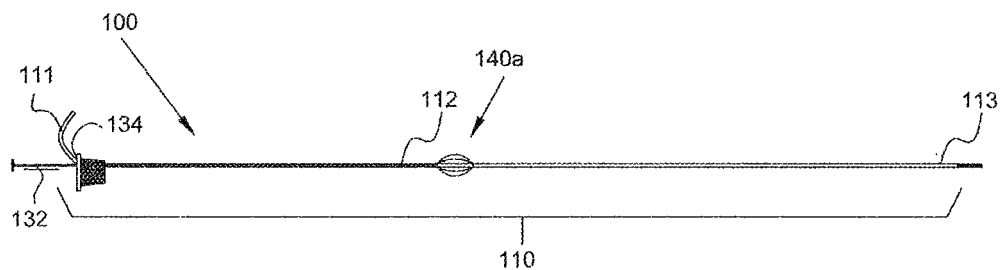
FIGS. 5A-5C illustrate side views of the scaffolding assembly of the present disclosure comprising three different expandable members.
Figure 5B:
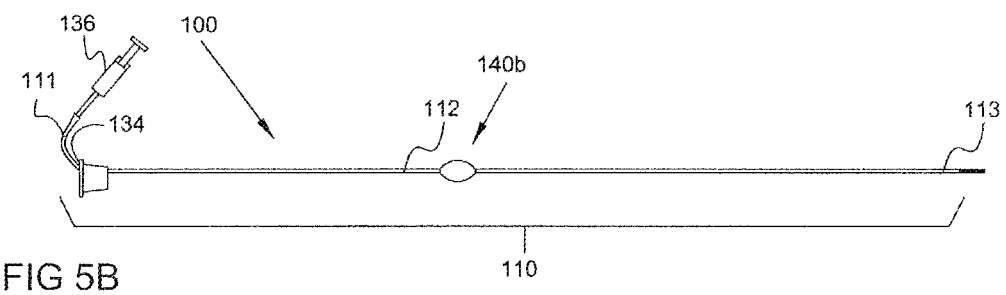
Figure 5C:
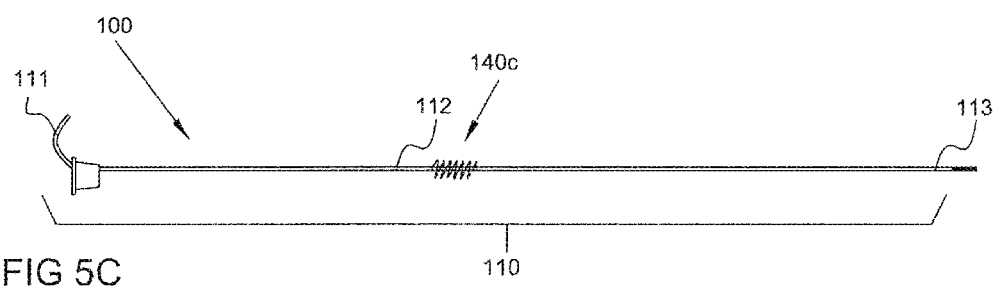

Referring now to FIGS. 5A, 5B, and 5C, three side views of three scaffolding assemblies of the present disclosure are illustrated comprising three different radially expandable members positioned at a mid portion of the shaft, each of which may be useful in maintaining a force upon the soft palate and/or base of the tongue. The force applied may be a full (i.e. 360°) or partial circumferential force to the airway, and will be configured to allow air to pass through the airway when the radially expandable member is expanded. Expandable members 140a, 140b and 140c of FIGS. 5A, 5B and 5C respectively, are disposed about shaft 110 which comprises proximal portion 111, mid portion 112, and distal portion 113. In a preferred embodiment, the expandable member may be positioned such that the expandable member is proximate to a patient's soft palate or base of tongue when scaffolding assembly 100 is inserted. The expandable member may surround shaft 110, or may be positioned along a partial circumference about the outer diameter of shaft 110. The expandable member is configured to be of minimal diameter prior to expansion, such as a diameter approximating the diameter of mid portion 112. When expanded, the expandable member typically has a diameter between 0.10 inches and 0.80 inches, more typically a diameter between 0.35 inches and 0.45 inches. The expandable member typically has an expanded length between 0.5 inches and 2.0 inches, more typically a length between 1.0 inches and 1.5 inches. In one embodiment, a kit of scaffolding assemblies 100 are provided including having a range of diameters and lengths configured to meet the needs of a group of patients with different anatomical geometries.

Referring specifically to FIG. 5A, scaffolding assembly 100 includes cage 140a whose proximal end is operably connected to rod 132. Proximal end 111 comprises lumen 134 configured to slidingly received rod 132. Rod 132 protrudes from the nosepiece 120 such that rod 132 can be advanced to radially expand cage 140a. In alternative embodiment, not shown, rod 132 is operably attached to distal end of cage 140a such that retraction of rod 132 causes cage 140a to expand. Movement of shaft 110 during expansion of cage 140a may be prevented by the patient or other user holding nosepiece 120 in place. Alternatively or additionally, a jaw attachment assembly, not shown but similar to mouthpiece 150 of FIG. 2, may be secured to the patient's jaw and attached to the distal end 113 of shaft 110. In an alternative embodiment, rod 132 is not included and cage 140a is a shaped memory component configured to radially expand from a near linear shape to the expanded cage shown in FIG. 5A when cage 140a transitions above room temperature.

Referring specifically to FIG. 5B, the expandable member comprises balloon 140b, such that a syringe 136 can be attached to the proximal end of shaft 110, and deliver a liquid or a gas into lumen 134, which is in fluid communication with balloon 140b, such that balloon 140b can be inflated to apply a scaffolding force to a portion of a patient's airway.

Referring specifically to FIG. 5C, the expandable member comprises a shaped memory component, coil 140c shown in its expanded helical state. Coil 140c may comprise a Nitinol material, and may be expanded by body heat or other thermal change such as a thermal change accomplished by passing an electric current through coil 140c. Additionally or alternatively, shaped memory component 140c may be constructed and arranged to transition to a non-helical radially expanded geometry. In an alternative embodiment, coil 140c is transitioned to an expanded state by application of a force, such as a twisting force applied by a rod similar to the rod 132 of FIG. 5A.

Figure 6:
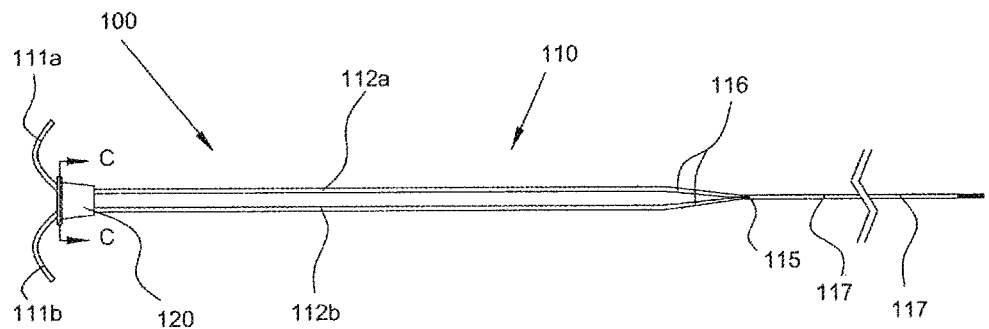
FIGS. 6 and 6A illustrate top views of an exemplary embodiment of the scaffolding assembly of the present disclosure.
Figure 6A:
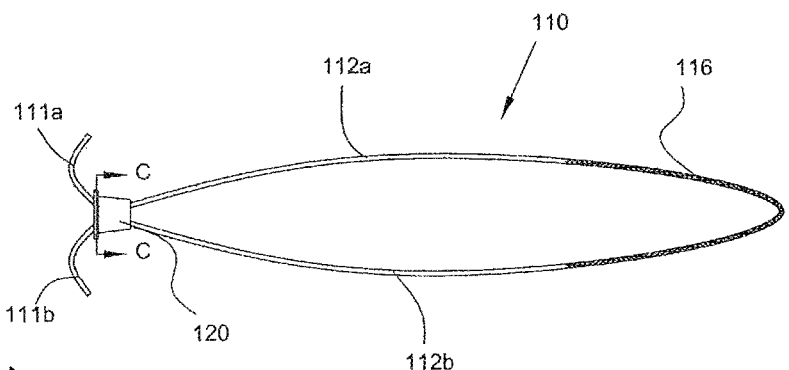

Referring now to FIG. 6, a top view of the airway scaffolding assembly of the present disclosure is illustrated wherein the shaft comprises a continuous loop having two proximal portions, a looped end, and a feeder filament. Scaffolding assembly 100 includes shaft 110 comprising proximal portions 111a and 111b each attached at their distal end to looped end 116. Feeder 117, a flexible filament, is attached to looped end 116 via coupling 115, typically a resiliently biased opening in the proximal end of feeder 117 configured to frictionally engage looped end 116. Looped end 116 can be passed through the nostril and the nasal passageway, after which feeder 117 can be detached by application of sufficient tensioning force or by cutting, such as via a cutting element similar to that in FIG. 8A herebelow. In this embodiment, proximal portions 111a and 111b are arranged to be placed in a single nosepiece, 120. In an alternative embodiment, proximal portions 111a is placed in a first nosepiece, positioned in a first nostril and proximal portion 111b is placed in a second nosepiece, positioned in a second nostril. Feeder 117 is inserted into the patient's nostril and through the airway behind the soft palate to an area proximate the patient's uvula. Feeder 117 may be captured by a capture probe, such as probe 200 of FIG. 2, such that looped end 116 can be attached to a jaw attachment assembly such as mouthpiece 150, also of FIG. 2. In an alternative embodiment, looped end 116 is cut to create two ends which can be independently fixed to a mouthpiece. Feeder 117 may be fixed to shaft 110, such as to remain in place while the patient sleeps. Alternatively, feeder 117 may be removably attached to shaft 110, such that it can be removed after insertion into the patient's airway but prior to sleeping. The detached configuration with feeder 117 removed is illustrated in FIG. 6A.

Figure 6B:
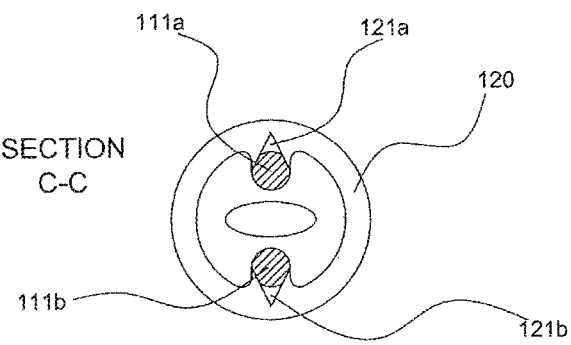
FIG. 6B illustrates a cross-sectional view of a nostril fixation element of the present disclosure in accordance with FIGS. 6 and 6A.

Referring to FIG. 6B, a cross-sectional view the nostril fixation element of FIG. 6, comprising two filament capture elements, is illustrated. Nosepiece 120 comprises notches 121a and 121b configured to capture and secure the proximal portions 111a and 111b. Notches 121a and 121b are further configured to allow the patient or another operator to tension shaft 110 such that the force applied to a portion of a patient's airway can be adjusted. In an alternative embodiment, scaffolding assembly 100 may comprise two nosepieces 120 with one nosepiece located in each nostril of the patient. For example, each nosepiece can include a notch, and an elongate member is inserted through each nostril independently, such as to independently attach to a jaw fixation device or to be joined to each other and then attached to a jaw fixation device.

Figure 7:
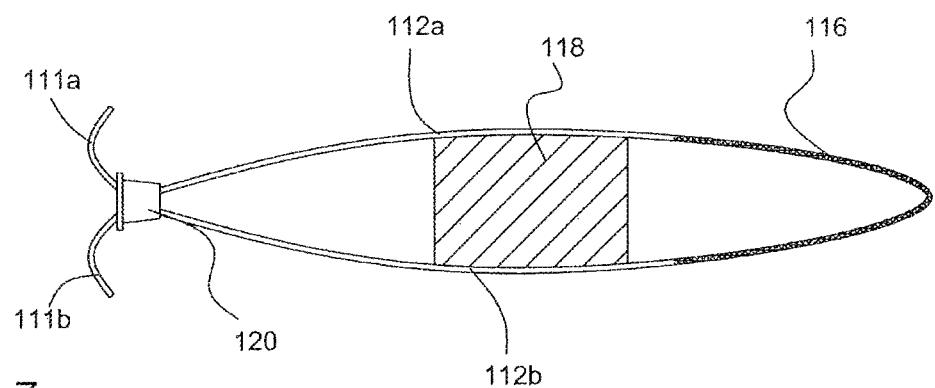
FIG. 7 illustrates a top view of an exemplary embodiment of a scaffolding assembly of the present disclosure.

Mid portions 112a and 112b and/or looped end 116 are constructed and arranged to be positioned on either side of the patient's uvula, such that mid portion 112a applies a force to a first location on the patient's soft palate and mid portion 112b applies a force to a second soft palate location, separate from the first soft palate location. In an alternative embodiment shown in FIG. 7, a sheet of material, membrane 118 is placed between two opposing segments of mid portion 112a and 112b. Membrane 118 is constructed and arranged to apply a force to the area of the soft palate positioned between the membrane-attached segments of mid portion 112a and 112b. Membrane 118 is typically made of a flexible material, such as a silicone or other elastomer, and typically comprises a surface area of at least 4 mm$^2$. In one embodiment, membrane 118 comprises a surface area of at least 10 mm$^2$. Membrane 118 may comprise a solid material, or may have a mesh or other porous construction.

Figure 8A:
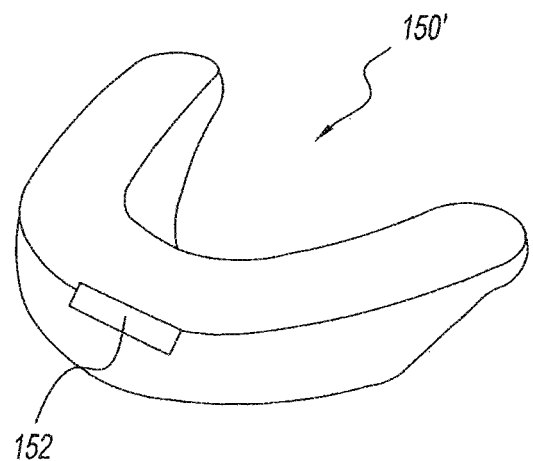
FIGS. 8A and 8B illustrate exemplary embodiments of a jaw attachment assembly of the present disclosure.
Figure 8B:
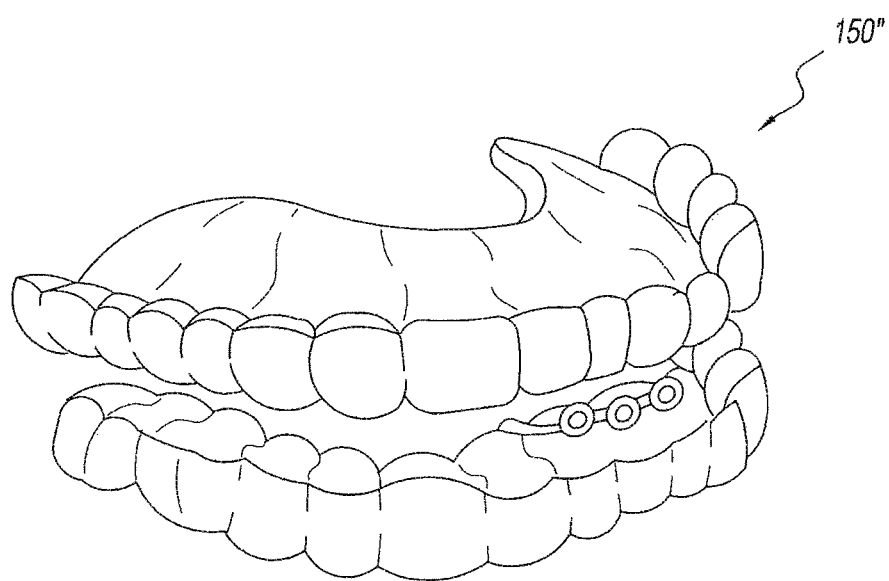

Referring now to FIGS. 8A and 8B, two alternative embodiments of the jaw attachment assembly of the present disclosure are illustrated including, respectively, a lower jaw attachment assembly and a device that attaches to both the upper and lower jaws. Mouthpiece 150' of FIG. 8A is attached to the patient's lower jaw and may comprise cutter 152. Cutter 152 is configured to remove the distal end of a shaft or other elongate member, not shown but typically the elongate shaft whose mid portion applies a force to a portion to the patient's airway. After being placed through the nostril, into the oropharynx region, into the mouth and threaded through mouthpiece 150', it may be desirable to remove excess portions of the shaft. Removing the distal end of the shaft may provide more comfort to a patient as well as improved cosmesis.

Mouthpiece 150" of FIG. 8B attaches to the patient's upper and lower jaws and may comprise a mandibular advancement device, such as the Thornton Adjustable Positioner (TAP®), manufactured by Aztec Orthodontic Laboratory, Inc. located in Tucson, Ariz., or a similar device configured to advance the mandible in an anterior direction, such as to move the base of the tongue to further prevent airway occlusion.

Figure 9A:
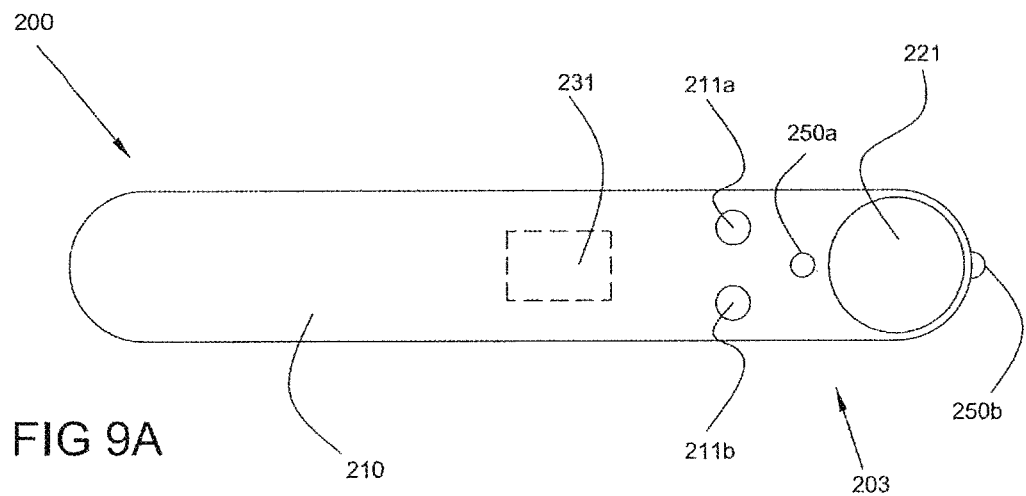
FIGS. 9A and 9B illustrate a top and side view, respectively, of a filament capture probe of the present disclosure.
Figure 9B:
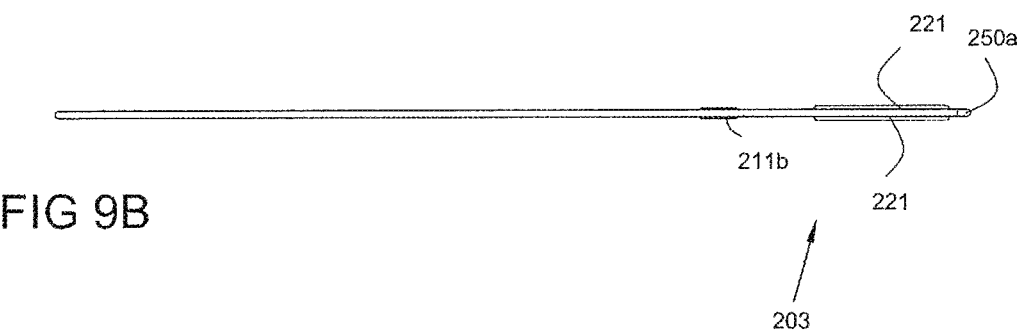

Referring now to FIGS. 9A and 9B, top and side views, respectively, of a filament capture probe of the present disclosure are illustrated. Probe 200 comprises a tongue depressor 210. Probe 200 further comprises a capture element, magnet 221, located proximate the distal end of tongue depressor 210, and configured to capture a portion (e.g., the distal end) of a shaft inserted through the nostril and into an airway of a patient. Alternative or in addition to magnet 221, other capture elements may be included such as: electro-magnets, Velcro, suction ports, mechanical graspers, adhesive, or combinations of these, each constructed and arranged to capture a corresponding capturable element of the distal end of a scaffolding assembly of the present disclosure.

Probe 200 may further comprise one or more light producing elements, such as LEDs 250a and 250b, located on the distal portion 203 of tongue depressor 210 and which may be used to illuminate the nasopharynx region, the oropharynx region and/or the laryngopharynx region. When inserted into the patient's mouth, LED 250a is oriented to direct light in a superior direction and LED 250b is oriented to direct light in a posterior direction. A power source, battery 231 provides power to LEDs 250a and 250b. Probe 200 may further comprise contacts 211a and 211b, located on tongue depressor 210, which are capable of automatically activating LED 250a and/or 250b with tissue or salivary contact or proximity. In another embodiment, contacts 211 may latch LED 250a and/or 250b in the on position (e.g., with a latching relay) until the power source is depleted. In yet another embodiment of probe 200, a manual switch, not shown, but typically a single-pole single-throw switch mounted to tongue depressor 210, is placed in a series electrical connection with battery 231 for manual activation of LEDs 250a and 250b. Alternatively or additionally, LED 250a may be located on a mid portion or proximal portion of probe 200.

Figure 10A:
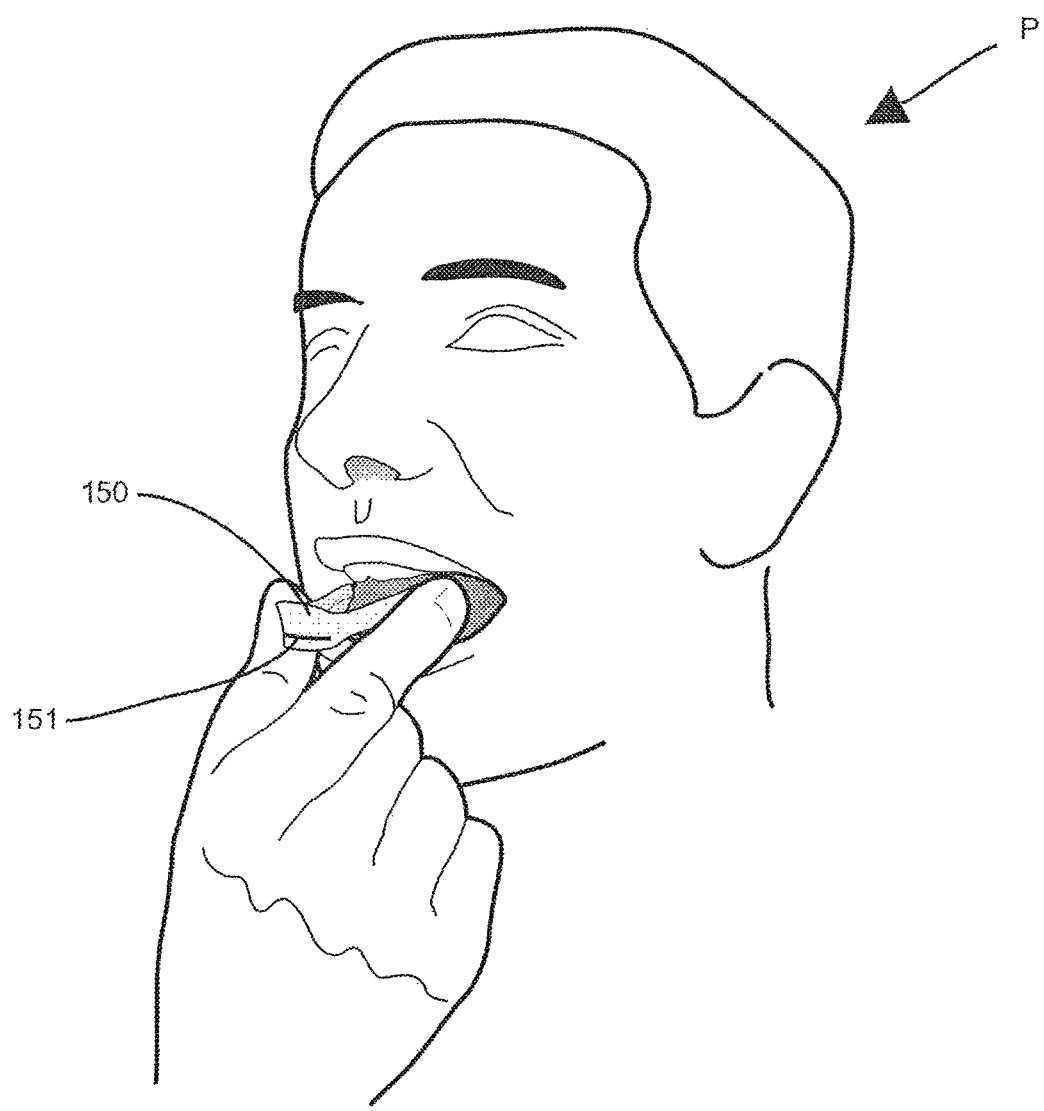
FIGS. 10A-10G illustrate a method of inserting an airway scaffolding apparatus of the present disclosure.

Referring now to FIGS. 10A-10G, a method of inserting an airway scaffolding apparatus of the present disclosure is illustrated. As shown in FIG. 10A, a patient P inserts mouthpiece 150, comprising slot 151 into the oral cavity to affix mouthpiece 150 to the upper jaw. In an alternative embodiment, jaw attachment assembly is attached to the lower jaw and/or both the lower and upper jaws.

Figure 10B:
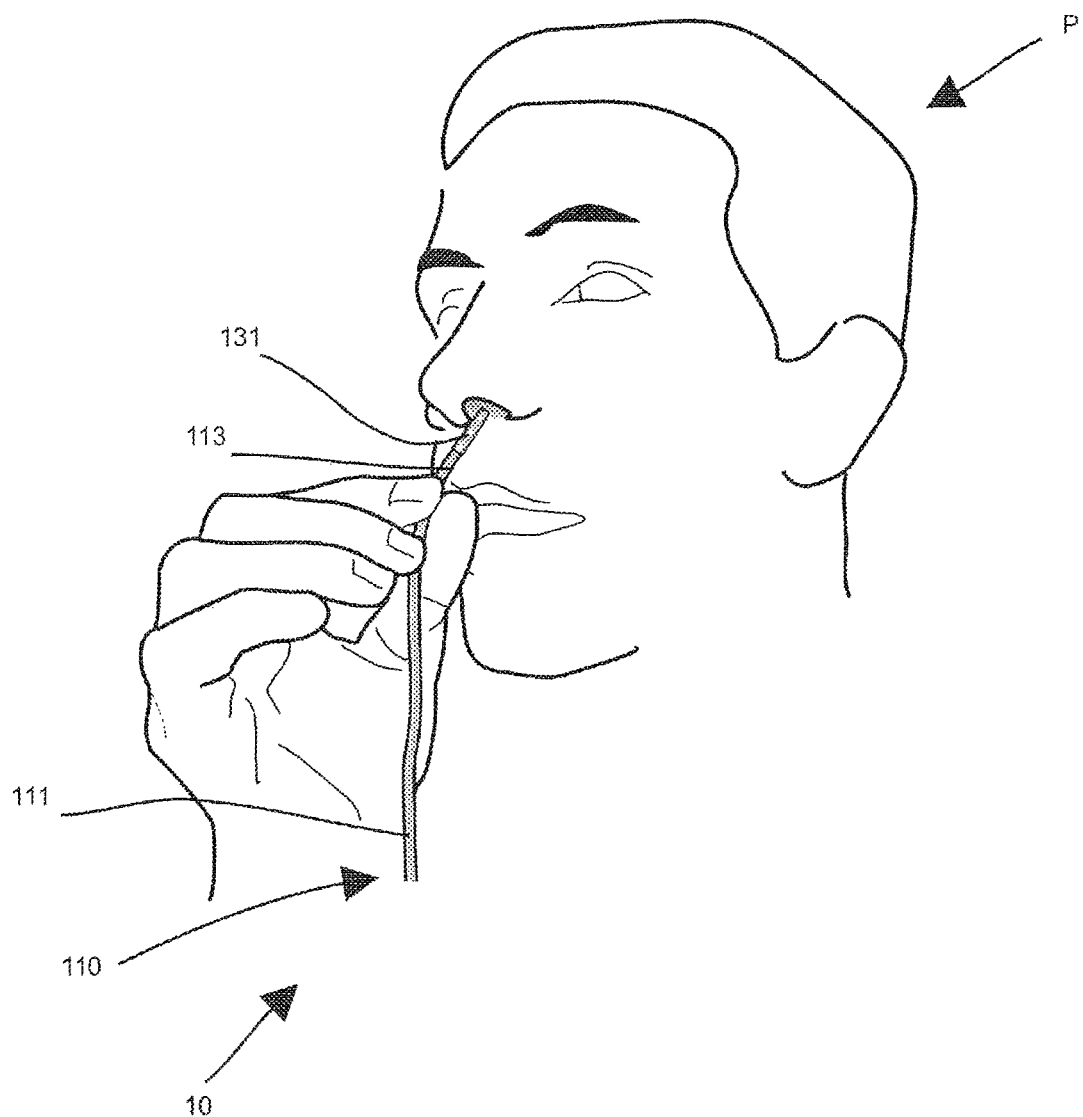

FIG. 10B depicts a step comprising the patient P inserting distal portion 113 of shaft 110, including magnetic material 131, into a nostril.

Figure 10C:
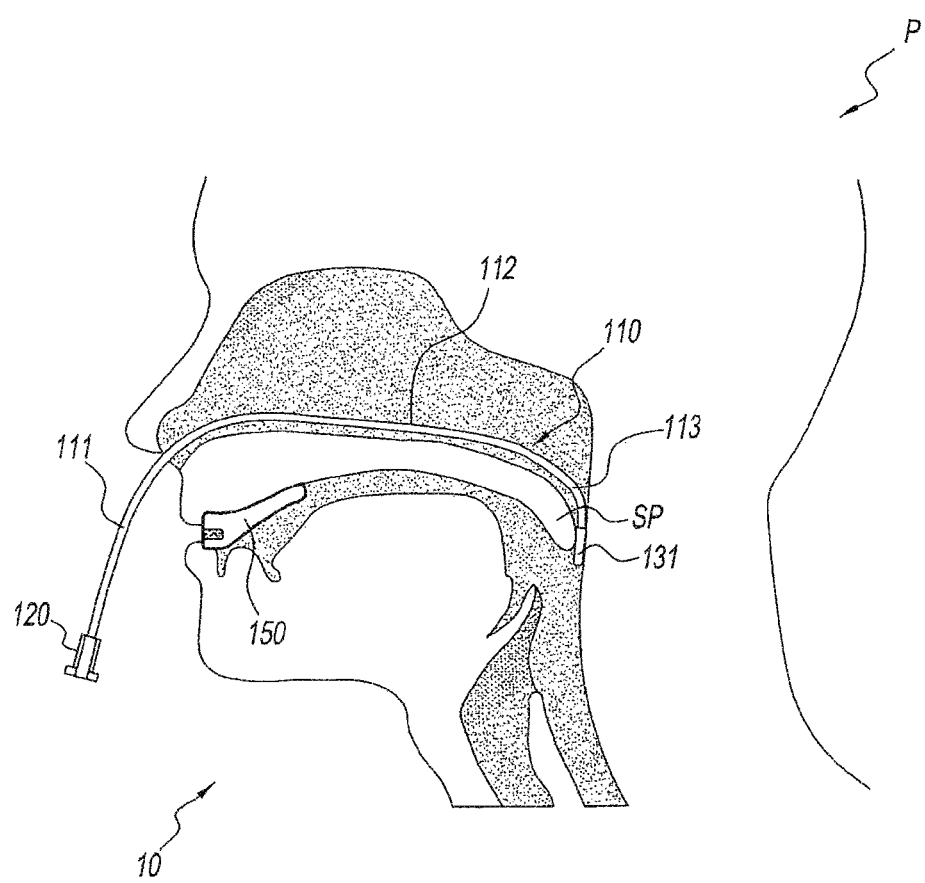

FIG. 10C depicts a step comprising the patient P threading shaft 110 through the nasal passageway so that magnetic material 131 is distal to patient P's soft palate SP.

Figure 10D:
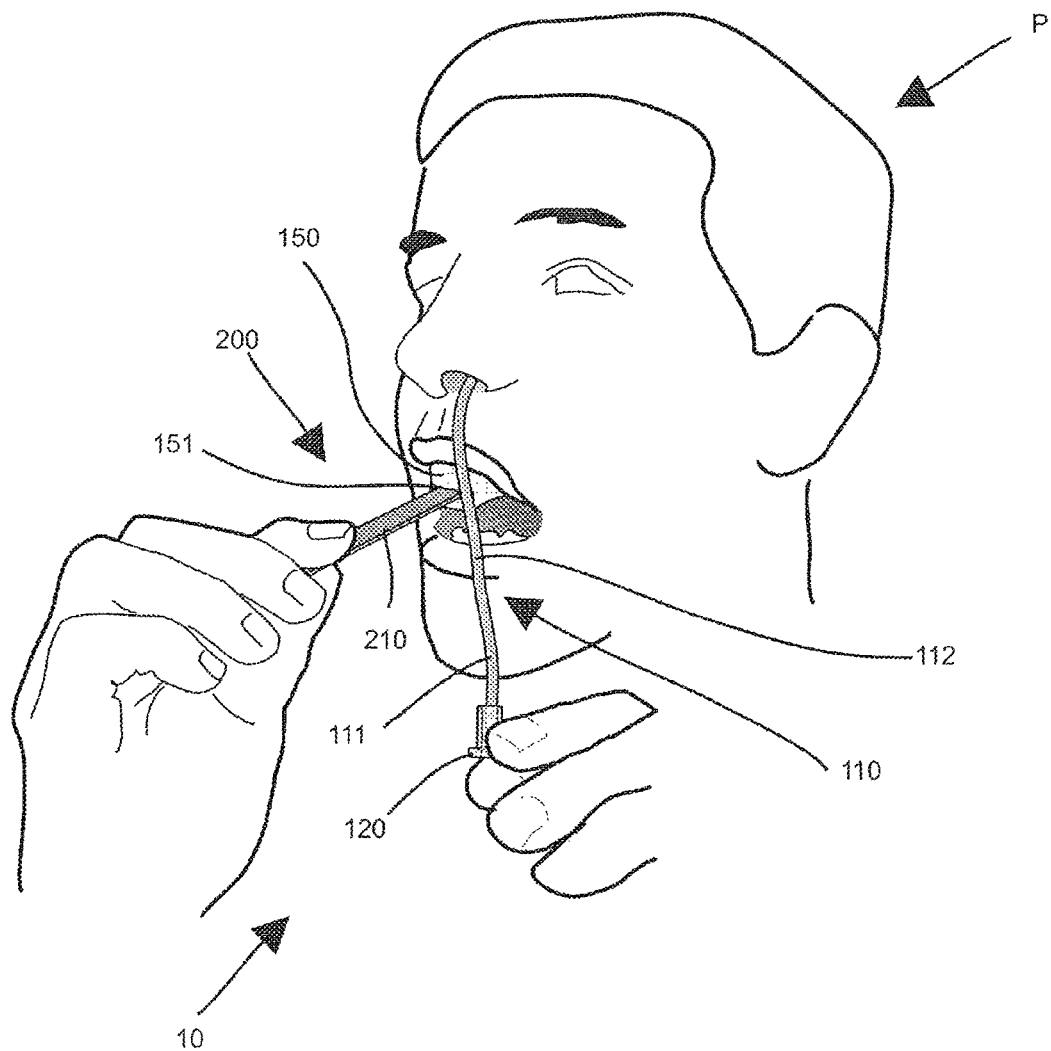

FIG. 10D depicts a step comprising patient P inserting probe 200 into slot 151 of mouthpiece 150 and beginning the capture of the distal end of shaft 110.

Patient P may hold proximal end 111, including nosepiece 120, while capturing the distal portion of shaft 110, magnetic material 131, such as to maintain the position of shaft 110.

Figure 10E:
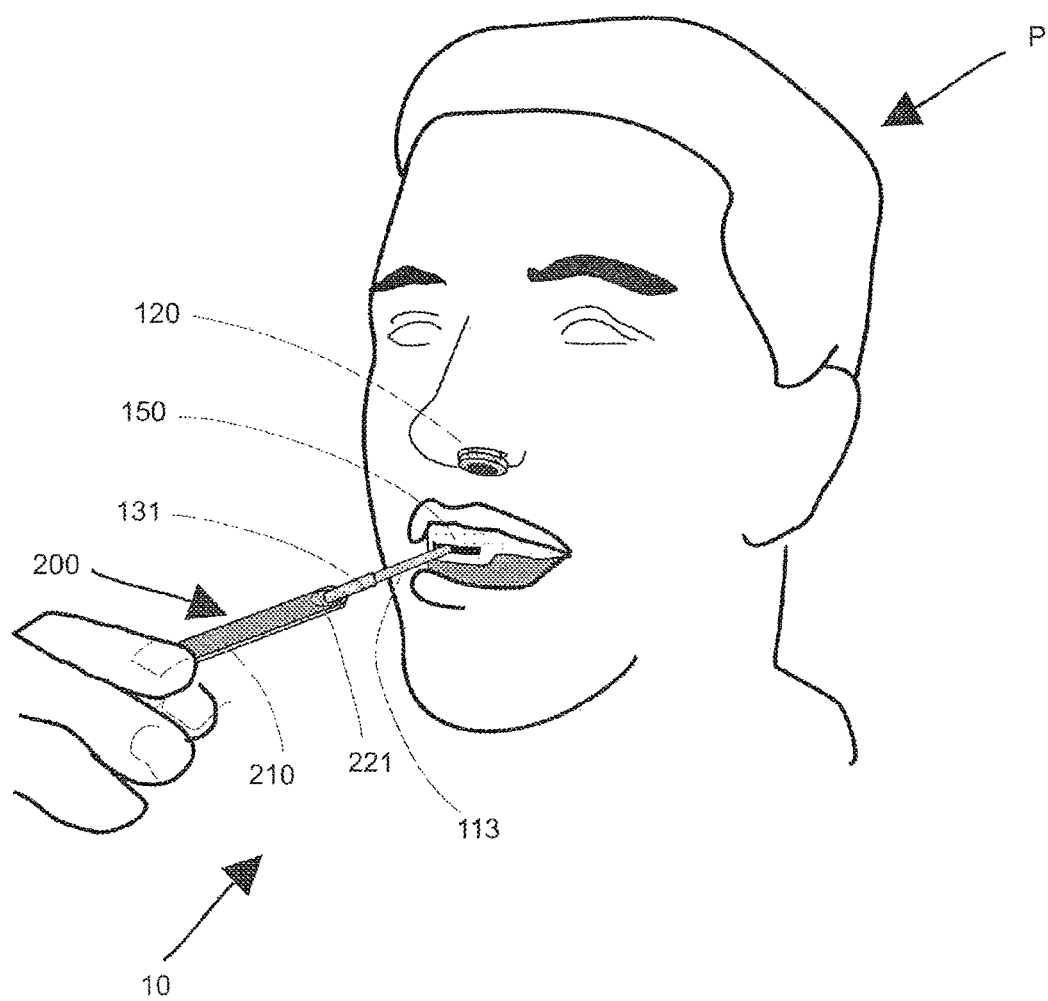

FIG. 10E depicts a step comprising patient P retrieving the captured magnetic material 131 and distal portion 113 of shaft 110 using magnet 221. Magnet 221, located on the distal end of probe 200, captures magnetic material 131 from the oropharynx region, while nosepiece 120 is secured in a nostril of the patient.

Figure 10F:
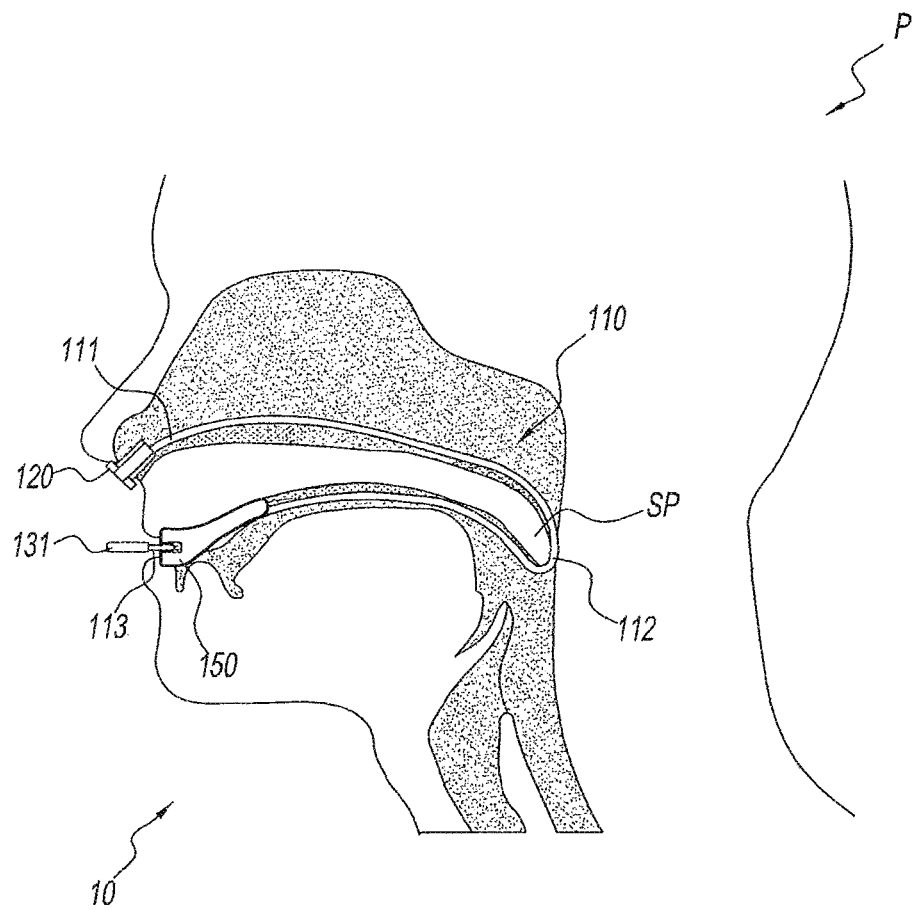

FIG. 10F depicts a side sectional view of the configuration of FIG. 10E with nosepiece 120 inserted into patient P's nostril, and distal portion 113 exiting mouthpiece 150. Here, shaft 110 has not yet been tensioned, such as tensioning caused by applying a force to proximal end 111 and/or distal end 113.

Figure 10G:
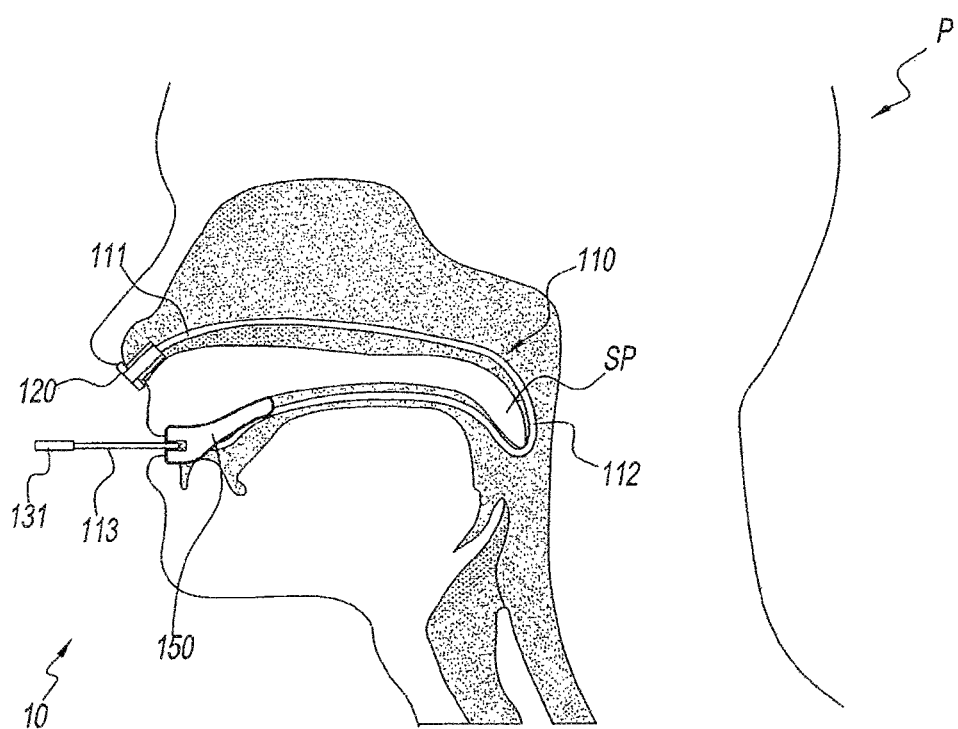

FIG. 10G depicts a step comprising tensioning shaft 110 by patient P retracting the distal portion 113 through mouthpiece 150 until a compressing force is applied by mid portion 112 to soft palate SP. Distal portion 113 may be captured in a notch or other frictionally engaging element, not shown but described in detail hereabove. Tensioning of shaft 110 has caused the tissue of soft palate SP to move in an anterior direction as compared to the soft palate SP tissue position of FIG. 10F. Proper tension in shaft 110 provides a sufficient opening in the airway proximate soft palate SP while avoiding patient P discomfort. After tensioning shaft 110, distal end 113 may or may not be removed, such as by a cutting element, not shown but integral to mouthpiece 150.

In one embodiment, an airway scaffolding apparatus is inserted into a patient in the serial order of FIGS. 10A through 10G. In an alternative embodiment, a different order is used, such as an order in which shaft 110 is inserted through the nostril of the patient prior to inserting mouthpiece 150 into the patient's mouth. In one embodiment, the distal end of shaft 110 is captured and affixed to mouthpiece 150 prior to inserting mouthpiece 150 into the patient's mouth. After use, such as after a night's sleep, apparatus 10 is removed, such as in a reverse order as described in reference to FIGS. 10A through 10G.

Figure 11:
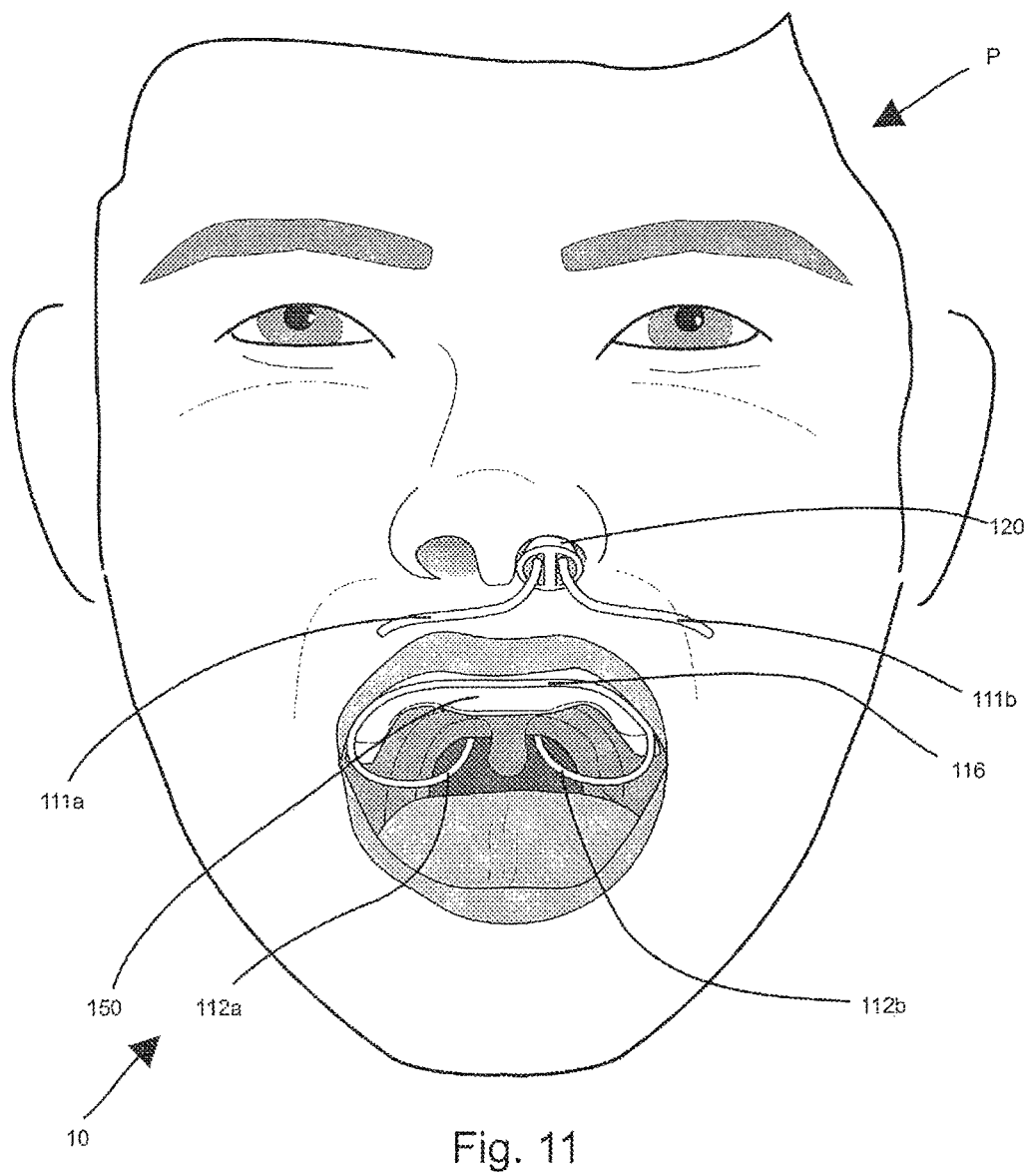
FIG. 11 illustrates an exemplary embodiment of an airway scaffolding apparatus of the present disclosure inserted within a patient.

Referring now to FIG. 11, an airway scaffolding apparatus of the present disclosure is illustrated with a scaffolding assembly inserted into the single nostril of a patient, with its looped end positioned on either side of the patient's uvula and fixed to a mouthpiece. Apparatus 10 includes scaffolding assembly 100 and mouthpiece 150. Scaffolding assembly 100 includes nosepiece 120 inserted into a single nostril with proximal ends 111a and 111b of shaft 110 located proximate the nostril. Looped end 116 is inserted into the nostril and into the oropharynx region such that mid portions 112a and 112b are positioned on either side of patient P's uvula. Looped end 116 is wrapped around the periphery of mouthpiece 150, and is secured to mouthpiece 150, such as via one or more grooves, hooks, clasps, Velcro, or other mechanical fasteners, all not shown. Tensioning is accomplished by pulling proximal portions 111a and/or 111b away from the patient's nostril, and capturing in one or more notches, not shown but described in detail hereabove.

Figure 12:
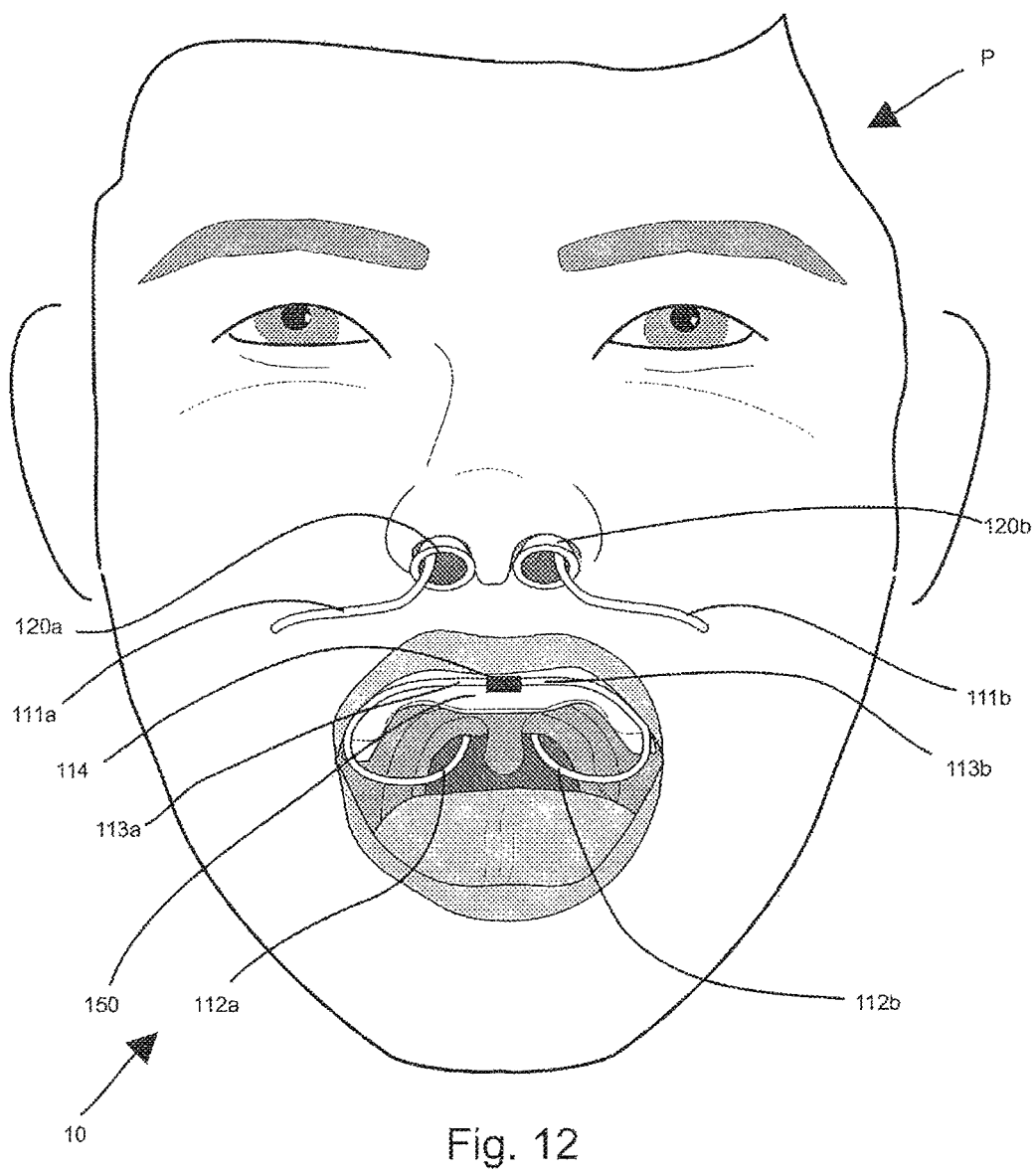
FIG. 12 illustrates another exemplary embodiment of an airway scaffolding apparatus of the present disclosure inserted within a patient.

Referring now to FIG. 12, an airway scaffolding apparatus of the present disclosure is illustrated, with a scaffolding assembly inserted into each of the patient's nostrils with its mid portion positioned on either side of the uvula and its distal ends fixed to a mouthpiece. Apparatus 10 includes scaffolding assembly 100 and mouthpiece 150. Scaffolding assembly 100 includes nosepieces 120a and 120b, each inserted into a nostril of patient P. Distal ends 113a and 113b are inserted into each nostril, traveling past the soft palate, separating to either side of the uvula, and into the mouth to be secured to mouthpiece 150, such as by being looped around mouthpiece 150 and attached together by a crimp or adhesive coupler, connector 114. Proximal portions 111a and 111b are shown exiting nosepieces 120a and 120b, respectively.

Looped end 116 is wrapped around the periphery of mouthpiece 150, and looped end 116 and/or connector 114 are secured to mouthpiece 150, such as via one or more grooves, hooks, clasps, Velcro, or other mechanical fasteners, all not shown. Tensioning is accomplished, independently or in unison, by pulling proximal portions 111a and/or 111b away from the patient's nostril, and capturing in one or more notches, not shown but described in detail hereabove.

Figure 13A:
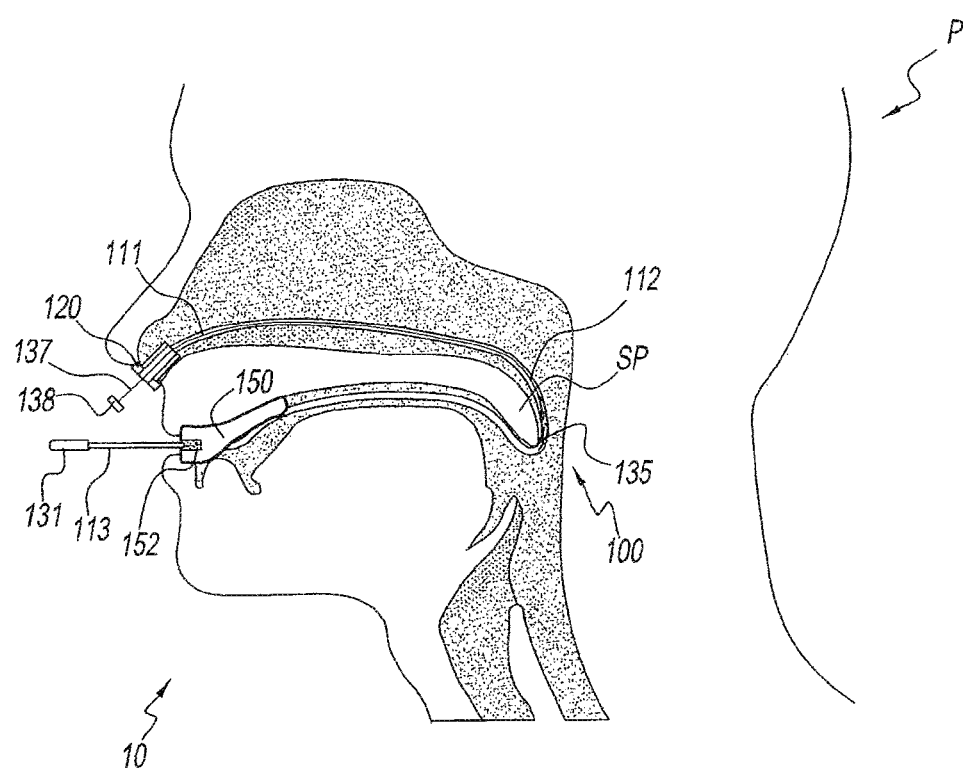
FIGS. 13A and 13B illustrate a cross-sectional profile view of an airway scaffolding apparatus of the present disclosure comprising an assembly with an expandable member inserted within a patient.
Figure 13B:
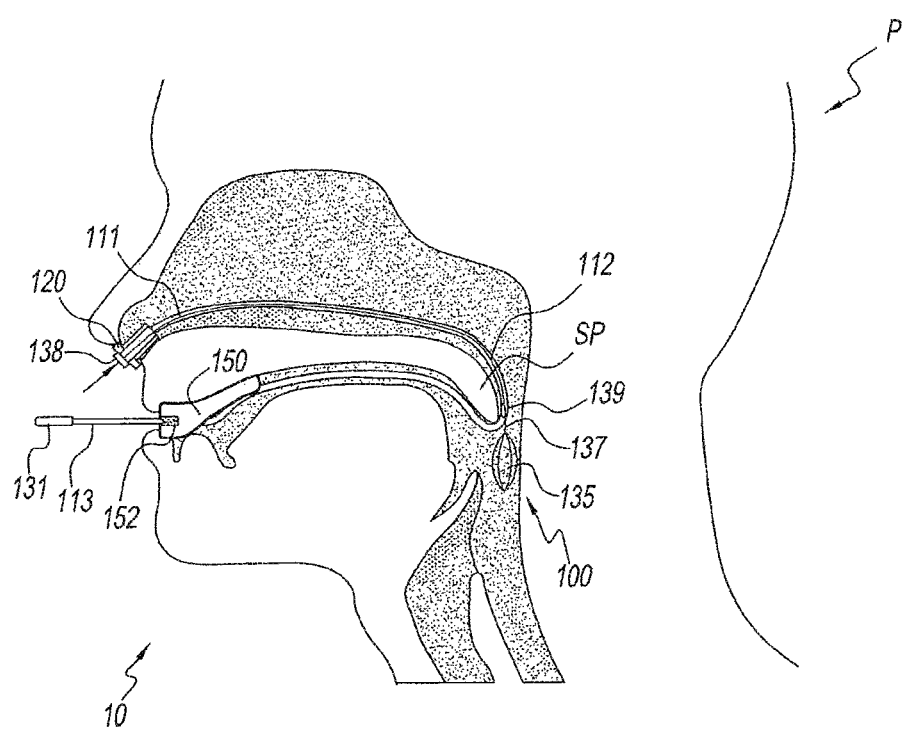

Referring now to FIGS. 13A and 13B, a cross-sectional profile view of an airway scaffolding apparatus comprising a device with an expandable member is shown inserted within a patient. FIG. 13A illustrates apparatus 10 including scaffolding assembly 100 and mouthpiece 150. Scaffolding assembly 100 comprises expandable member 135, shown in an unexpanded position in FIG. 13A and in an advanced position and radially expanded geometry in FIG. 13B. Expandable member 135 typically comprises an expandable cage such as a Nitinol cage or a balloon connected to one or more inflation lumens. Expandable member 135 is configured, when deployed, to exert a scaffolding force on the base of the patient's tongue to prevent airway occlusion by the tongue. The force applied may be a full (i.e. 360°) or partial circumferential force.

In one embodiment, expandable member 135 is a radially expandable cage that is attached to a shaft 137. Expandable member 135 is advanced by pushing on knob 138 to distally advance shaft 137. As expandable member 135 exits side hole 139, it automatically transforms to a radially expanded state. Shaft 137 may be slidingly attached to nosepiece 120, and it may be removable. Expandable member 135 may comprise a cage, balloon, or a shaped memory component as described in detail hereabove. Retraction of expandable member 135 may be accomplished by retraction of knob 138 and/or shaft 137, such as a retraction performed prior to the removal of apparatus 10.

Figure 14:
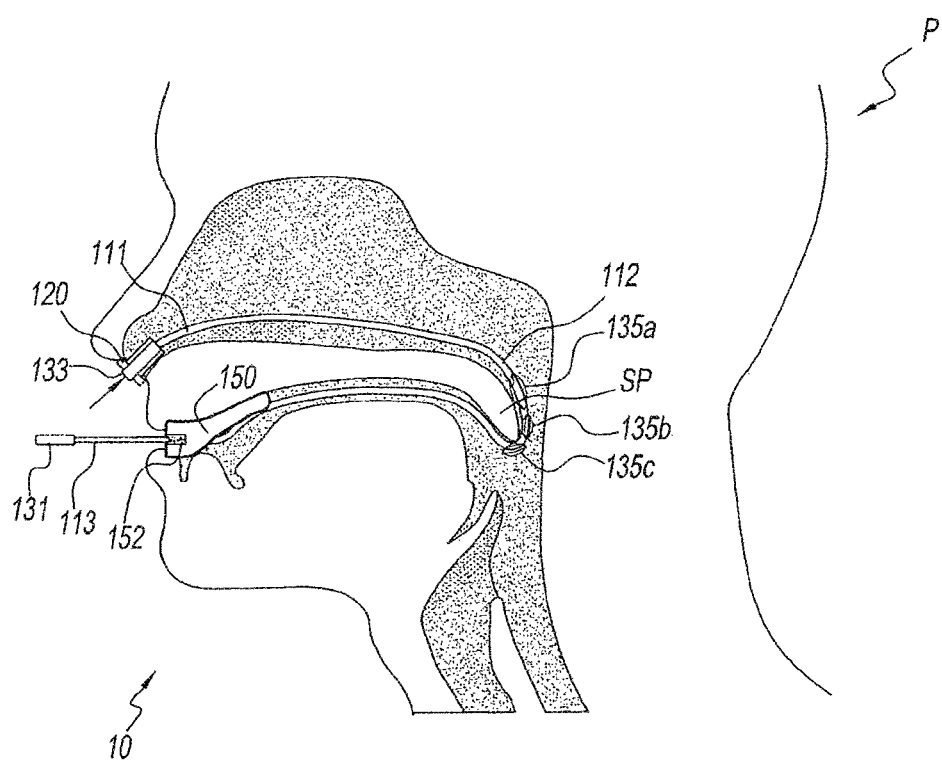
FIG. 14 illustrates a cross-sectional profile view of an airway scaffolding apparatus of the present disclosure comprising a plurality of expandable members inserted within a patient.

Referring now to FIG. 14, a cross-sectional profile view of an airway scaffolding apparatus comprising a device with a plurality of expandable members disposed about a shaft inserted within a patient's airway is illustrated. A plurality of expandable members 135a, 135b and 135c may be positioned along multiple points of a patient's airway to prevent airway narrowing or occlusion. For example, expandable members 135a and 135b may exert a force upon a patient's soft palate, while expandable member 135c exerts a force upon the base of a patient's tongue. Expandable members 135a, 135b and 135c may be deployed simultaneously or sequentially. In another embodiment, more than two expandable members may be utilized and deployed and/or expanded simultaneously or at varying times. In another embodiment, more than three expandable members may be utilized and deployed and/or expanded simultaneously or at varying times. The force applied by each expandable member may be a full (i.e. 360°) or partial circumferential force to the airway. Expandable members 135a, 135b, and 135c may comprise a cage, balloon, or shaped memory component and be deployed and radially expanded via mechanisms described in FIG. 5A-5C hereabove. In an alternative embodiment, shaft mid portion 112 may comprise a hole, not shown, such that expandable members 135a, 135b, and/or 135c may exit the hole and expand proximate a patient's soft palate. Expandable members 135a, 135b, and 135c may also be configured to compress and be recaptured into the hole.

Rod 133 protrudes from the nosepiece 120 such that rod 132 can be advanced to radially expand expandable members 135a-c, similar to the construction and functionality of rod 132 of FIG. 5A.

Figure 15A:
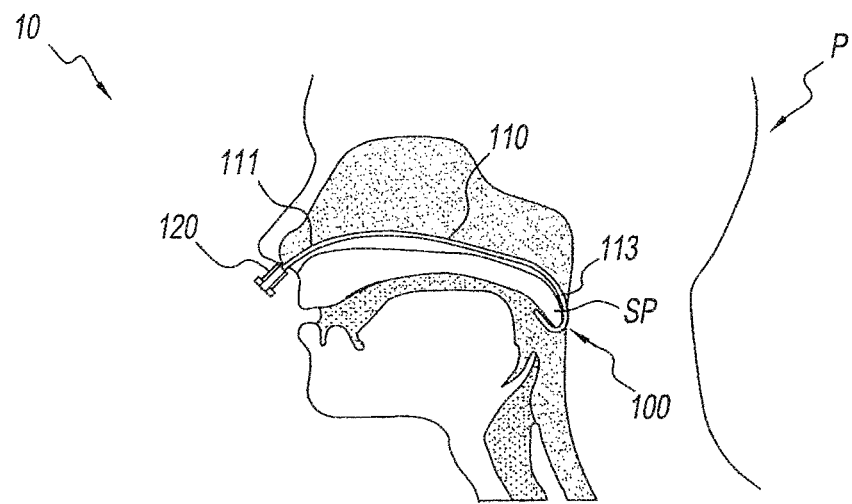
FIGS. 15A and 15B illustrate cross-sectional profile views of an airway scaffolding apparatus of the present disclosure comprising a hook-like distal end inserted within a patient.
Figure 15B:
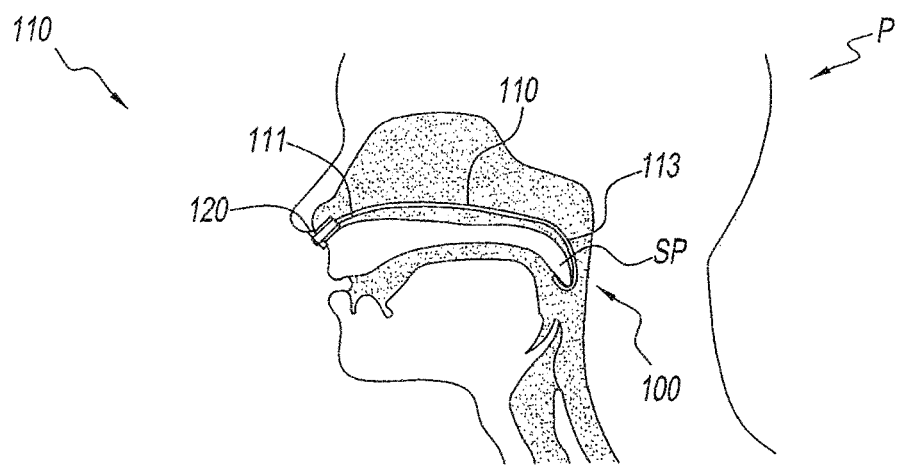

Referring now to FIGS. 15A and 15B, a cross-sectional profile view of an airway scaffolding apparatus of the present disclosure is illustrated comprising a device with a hook-like distal end inserted within an airway of a patient. FIG. 15A illustrates scaffolding assembly 100 inserted within the patient prior to tensioning scaffolding assembly 100, while FIG. 15B illustrates scaffolding assembly 100 in a tensioned state, applying force to the soft palate and thus preventing airway occlusion.

In this embodiment, scaffolding assembly 100 includes distal portion 113 of shaft 110 which is configured to frictionally engage the distal end of the soft palate to maintain its own relative position, such as in the hook configuration shown in FIGS. 15A and 15B. Here, distal portion 113 is sufficiently rigid such that it maintains its shape and position during sleep, avoiding the necessity of a mouthpiece or other separate distal attachment assembly. Distal portion 113 is configured to, under an appropriate amount of user applied tension, sufficiently straighten to allow atraumatic removal of shaft 110 through the nostril of patient P. Distal portion 113 may be plastically deformable, such as to be first deformed to maintain a hooked or curved shape during sleep, and subsequently deformed to a straightened shape prior to and/or during insertion and/or removal. Alternatively, distal portion 113 may be resiliently biased in the curved orientation shown in FIGS. 15A and 15B, such as a distal portion 113 including a resiliently biased shaped memory alloy such as Nitinol.

While the preferred embodiments of the apparatus, systems and methods have been described in reference to the environment in which they were developed, they are merely illustrative of the principles of the disclosures. Modification or combinations of the above-described assemblies, other embodiments, configurations, and methods for carrying out the disclosure, and variations of aspects of the disclosure that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth below not be construed as being order-specific unless such order specificity is expressly stated in the claim.

All of the patents, publications and other documents referred to herein are hereby incorporated by reference as if fully set forth in this application.

What is claimed is:

1. A method of scaffolding an airway of a patient, the method comprising:
    inserting an elongate member of an airway scaffolding apparatus into the patient airway, the airway scaffolding apparatus comprising:
        the elongate member comprising,
            a proximal portion with a proximal end;
            a distal portion with a distal end; and
            a middle portion positioned between the proximal portion and the distal portion;
        a first fixation element constructed and arranged to maintain the elongate member proximal portion in a relatively fixed position; and
        a second fixation element constructed and arranged to maintain the elongate member distal portion in a relatively fixed position;
    wherein the elongate member middle portion is constructed and arranged to apply a force to a portion of an airway.

2. The method according to claim 1, wherein the first fixation element comprises a nosepiece and the method further comprises inserting the nosepiece into a nostril of the patient.

3. The method according to claim 2, further comprising attaching the elongate member proximal portion to the nosepiece.

4. The method according to claim 2, wherein the nosepiece comprises a tensioner constructed and arranged to allow an operator to tension the elongate member.

5. The method according to claim 1, wherein the second fixation element comprises a mouthpiece and the method further comprises attaching the mouthpiece to at least one of an upper jaw or a lower jaw of the patient.

6. The method according to claim 5, further comprising attaching the elongate member distal portion to the mouthpiece.

7. The method according to claim 5, wherein the mouthpiece comprises a tensioner constructed and arranged to allow an operator to tension the elongate member.

8. The method according to claim 1, further comprising capturing the elongate member distal portion.

9. The method according to claim 8, wherein the elongate member distal portion is captured by a probe device inserted into a mouth of the patient.

10. The method according to claim 8, wherein the elongate member distal portion is captured with magnetic forces.

11. The method according to claim 1, wherein the portion of the patient's airway comprises a portion of a soft palate of the patient.

12. The method according to claim 1, further comprising applying an analgesic agent to at least a portion of the patient's airway.

13. The method according to claim 1, wherein the elongate member comprises at least one of a coated or a treated portion.

14. The method according to claim 1, wherein the elongate member middle portion is constructed and arranged to be radially expandable.

15. The method according to claim 1, wherein the elongate member middle portion is constructed and arranged to contact a soft palate of a patient.

* * * * *